US008420871B2

(12) United States Patent
Gilbeau et al.

(10) Patent No.: US 8,420,871 B2
(45) Date of Patent: Apr. 16, 2013

(54) PROCESS FOR PRODUCING AN ORGANIC COMPOUND

(75) Inventors: Patrick Gilbeau, Braine-le-Comte (BE); Ivan De Andolenko, Tavaux (FR); Philippe Krafft, Rhode Saint Genese (BE); Freddy Gielen, Rixensart (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 13/238,206

(22) Filed: Sep. 21, 2011

(65) Prior Publication Data
US 2012/0010420 A1 Jan. 12, 2012

Related U.S. Application Data

(63) Continuation of application No. 11/915,059, filed as application No. PCT/EP2006/062438 on May 19, 2006, now Pat. No. 8,067, 645.

(60) Provisional application No. 60/734,657, filed on Nov. 8, 2005, provisional application No. 60/734,637, filed on Nov. 8, 2005, provisional application No. 60/734,635, filed on Nov. 8, 2005, provisional application No. 60/734, 659, filed on Nov. 8, 2005, provisional application No. 60/734,634, filed on Nov. 8, 2005, provisional application No. 60/734,627, filed on Nov. 8, 2005, provisional application No. 60/734,658, filed on Nov. 8, 2005, provisional application No. 60/734,636, filed on Nov. 8, 2005.

(30) Foreign Application Priority Data

May 20, 2005 (EP) ..................................... 05104321
May 20, 2005 (FR) ...................................... 05 05120

(51) Int. Cl.
| C07C 31/34 | (2006.01) |
| C08F 16/02 | (2006.01) |
| C08F 283/00 | (2006.01) |
| C07D 301/24 | (2006.01) |

(52) U.S. Cl.
USPC ........ 568/844; 568/841; 525/328.8; 525/507; 549/520

(58) Field of Classification Search .................. 568/841, 568/844; 525/328.8, 507; 549/534, 520
See application file for complete search history.

(56) References Cited

U.S. PATENT DOCUMENTS

| 280,893 A | 7/1883 | Baujard |
| 865,727 A | 9/1907 | Queneau |

(Continued)

FOREIGN PATENT DOCUMENTS

| BE | 422877 | 8/1937 |
| CN | 1296003 a | 5/2001 |

(Continued)

OTHER PUBLICATIONS

Azeotropic Data-III Compiled by Lee H. Horsley, The Dow Chemical Co., Midland, Mich., American Chemical Society (1973).

(Continued)

*Primary Examiner* — Taylor Victor Oh
(74) *Attorney, Agent, or Firm* — Oblon, Spivak, McClelland, Maier & Neustadt, L.L.P.

(57) ABSTRACT

Process for producing a chlorohydrin by reaction between a multihydroxylated-aliphatic hydrocarbon, an ester of a multihydroxylated-aliphatic hydrocarbon, or a mixture thereof, and a chlorinating agent, according to which the multihydroxylated-aliphatic hydrocarbon, the ester of a multihydroxylated-aliphatic hydrocarbon, or the mixture thereof used contains at least one solid or dissolved metal salt, the process comprising a separation operation to remove at least part of the metal salt.

18 Claims, 1 Drawing Sheet

U.S. PATENT DOCUMENTS

| | | |
|---|---|---|
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Hermann |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,879,180 A | 4/1975 | Hutgens et al. |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,309,394 A | 1/1982 | Hudson |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,560,812 A | 12/1985 | Blytas |
| 4,595,469 A | 6/1986 | Foller |
| 4,599,178 A | 7/1986 | Blytas |
| 4,609,751 A | 9/1986 | Hajjar |
| 4,634,784 A | 1/1987 | Nagato et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer, Jr. et al. |
| 5,567,359 A | 10/1996 | Cassidy et al. |
| 5,578,740 A | 11/1996 | Au et al. |
| 5,710,350 A | 1/1998 | Jeromin et al. |
| 5,731,476 A | 3/1998 | Shawl et al. |
| 5,744,655 A | 4/1998 | Thomas et al. |
| 5,779,915 A | 7/1998 | Becker et al. |
| 5,908,946 A | 6/1999 | Stern et al. |
| 5,993,974 A | 11/1999 | Fukushima et al. |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,719,957 B2 | 4/2004 | Brady, Jr. et al. |
| 6,740,633 B2 | 5/2004 | Norenberg et al. |
| 6,806,396 B2 | 10/2004 | Gelblum et al. |
| 7,126,032 B1 | 10/2006 | Aiken |
| 7,128,890 B2 | 10/2006 | Ollivier |
| 7,557,253 B2 | 7/2009 | Gilbeau |
| 7,584,629 B2 | 9/2009 | Sohn et al. |
| 7,615,670 B2 | 11/2009 | Gilbeau |
| 7,893,193 B2 | 2/2011 | Krafft et al. |
| 7,906,691 B2 | 3/2011 | Krafft et al. |
| 7,906,692 B2 | 3/2011 | Krafft et al. |
| 7,939,696 B2 | 5/2011 | Krafft et al. |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel, Jr. |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0293707 A1 | 12/2007 | Wolfert et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0194847 A1 | 8/2008 | Krafft et al. |
| 2008/0194850 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0032617 A1 | 2/2010 | Gilbeau et al. |
| 2010/0105862 A1 | 4/2010 | Krafft et al. |
| 2010/0105964 A1 | 4/2010 | Krafft et al. |
| 2010/0168379 A1 | 7/2010 | Krafft et al. |
| 2010/0170805 A1 | 7/2010 | Krafft et al. |
| 2010/0179300 A1 | 7/2010 | Boulos et al. |
| 2010/0179302 A1 | 7/2010 | Krafft et al. |
| 2010/0212540 A1 | 8/2010 | Bobet et al. |
| 2010/0294727 A1 | 11/2010 | Gilbeau et al. |
| 2010/0305367 A1 | 12/2010 | Borremans |
| 2010/0311942 A1 | 12/2010 | Gilbeau et al. |
| 2011/0028683 A1 | 2/2011 | Gilbeau et al. |
| 2011/0152545 A1 | 6/2011 | Balthasart et al. |
| 2011/0166369 A1 | 7/2011 | Krafft et al. |
| 2011/0172449 A1 | 7/2011 | Krafft et al. |

FOREIGN PATENT DOCUMENTS

| | | |
|---|---|---|
| CN | 101041421 | 9/2007 |
| DE | 58396 | 8/1891 |
| DE | 197 308 | 11/1906 |
| DE | 238 341 | 3/1908 |
| DE | 869 193 | 3/1953 |
| DE | 1 041 488 | 10/1958 |

| | | | | | |
|---|---|---|---|---|---|
| DE | 1 075 103 | 2/1960 | GB | 984 633 | 3/1965 |
| DE | 1 226 554 | 10/1966 | GB | 1 387 668 | 3/1972 |
| DE | 2 241 393 | 2/1974 | GB | 1286893 | 8/1972 |
| DE | 25 21 813 | 12/1975 | GB | 1 493 538 | 4/1975 |
| DE | 30 03 819 | 8/1981 | GB | 1 414 976 | 11/1975 |
| DE | 216 471 | 6/1983 | GB | 2 173 496 | 10/1986 |
| DE | 32 43 617 | 5/1984 | GB | 702143 | 10/1990 |
| DE | 37 21 003 | 6/1987 | GB | 2 336 584 | 10/1999 |
| DE | 43 02 306 | 8/1994 | HU | 2002-003023 | 3/2004 |
| DE | 43 35 311 | 4/1995 | JP | 39-27230 | 11/1928 |
| DE | 102 03 914 | 1/2002 | JP | 50-062909 | 5/1975 |
| DE | 102 154 709 | 6/2004 | JP | 55-041858 | 3/1980 |
| DE | 238341 | 3/2008 | JP | 56-29572 | 3/1981 |
| DE | 197 309 | 4/2008 | JP | 56-99432 | 8/1981 |
| EP | 0 296 341 | 12/1988 | JP | 56-155009 | 12/1981 |
| EP | 0 347 618 | 12/1989 | JP | 60-258171 | 12/1985 |
| EP | 0 421 379 | 4/1991 | JP | 61-044833 | 3/1986 |
| EP | 0 452 265 | 10/1991 | JP | 61-112066 | 5/1986 |
| EP | 0 518 765 | 12/1992 | JP | 61-140532 | 6/1986 |
| EP | 0 522 382 | 1/1993 | JP | 61-236749 | 10/1986 |
| EP | 0 535 949 | 4/1993 | JP | 62-242638 | 10/1987 |
| EP | 0 563 720 | 10/1993 | JP | 63-195288 | 8/1988 |
| EP | 0 568 389 | 11/1993 | JP | 2-137704 | 5/1990 |
| EP | 0 582 201 | 2/1994 | JP | 3-223267 | 10/1991 |
| EP | 0 618 170 | 10/1994 | JP | 03-223267 | 10/1991 |
| EP | 0 916 624 | 5/1999 | JP | 04-089440 | 3/1992 |
| EP | 0 919 551 | 6/1999 | JP | 04-217637 | 8/1992 |
| EP | 0 774 450 | 2/2000 | JP | 03-014527 | 1/1994 |
| EP | 1 059 278 | 12/2000 | JP | 06-009589 | 1/1994 |
| EP | 1 106 237 | 6/2001 | JP | 6-25196 | 4/1994 |
| EP | 1 153 887 | 11/2001 | JP | 6-184024 | 7/1994 |
| EP | 1 163 946 | 12/2001 | JP | 06-321852 | 11/1994 |
| EP | 1 231 189 | 8/2002 | JP | 08-003087 | 1/1996 |
| EP | 1 298 154 | 4/2003 | JP | 8-59593 | 3/1996 |
| EP | 0 561 441 | 9/2003 | JP | 09-299953 | 11/1997 |
| EP | 1 411 027 | 4/2004 | JP | 10-139700 | 5/1998 |
| EP | 1 752 435 | 2/2007 | JP | 10-218810 | 8/1998 |
| EP | 1 752 436 | 2/2007 | JP | 2000-344692 | 12/2000 |
| EP | 1 760 060 | 3/2007 | JP | 2001-037469 | 2/2001 |
| EP | 1 762 556 | 3/2007 | JP | 2001-213827 | 8/2001 |
| EP | 1 770 081 | 4/2007 | JP | 2001-126581 | 9/2001 |
| EP | 1 772 446 | 4/2007 | JP | 2001-261308 | 9/2001 |
| EP | 1 775 278 | 4/2007 | JP | 2001-276572 | 10/2001 |
| EP | 2 085 364 | 8/2009 | JP | 2002-02033 | 1/2002 |
| FR | 1 306 231 | 10/1961 | JP | 2002-038195 | 2/2002 |
| FR | 1 417 388 | 10/1964 | JP | 2002-265986 | 9/2002 |
| FR | 1 476 073 | 4/1966 | JP | 2002-363153 | 12/2002 |
| FR | 1 577 792 | 8/1968 | JP | 2003-81891 | 3/2003 |
| FR | 2 180 138 | 5/1973 | JP | 2003-89680 | 3/2003 |
| FR | 2 217 372 | 2/1974 | JP | 2003-183191 | 7/2003 |
| FR | 2 565 229 | 12/1985 | JP | 2003-206473 | 7/2003 |
| FR | 2 752 242 | 2/1998 | JP | 2004-518102 | 6/2004 |
| FR | 2 862 644 | 5/2005 | JP | 2004-216246 | 8/2004 |
| FR | 2 868 419 | 10/2005 | JP | 2005-007841 | 1/2005 |
| FR | 2 869 612 | 11/2005 | JP | 2005-097177 | 4/2005 |
| FR | 2 869 613 | 11/2005 | JP | 76021635 | 4/2005 |
| FR | 2 872 504 | 1/2006 | JP | 2005-513064 | 5/2005 |
| FR | 2 881 732 | 8/2006 | JP | 2007-008898 | 1/2007 |
| FR | 2 885 903 | 11/2006 | JP | 2009-263338 | 11/2009 |
| FR | 2 912 743 | 8/2008 | KR | 900006513 | 11/1987 |
| FR | 2 913 683 | 9/2008 | KR | 2003-29740 | 5/2003 |
| FR | 2 917 411 | 12/2008 | KR | 10-0514819 | 11/2004 |
| FR | 2 918 058 | 1/2009 | SU | 123153 | 1/1959 |
| FR | 2 925 045 | 6/2009 | SU | 1125226 | 11/1984 |
| FR | 2 929 611 | 10/2009 | SU | 1159716 | 6/1985 |
| FR | 2 935 699 | 3/2010 | SU | 1685969 | 10/1991 |
| FR | 2935 968 | 3/2010 | WO | WO 95/14639 | 6/1995 |
| GB | 14 767 | 0/1914 | WO | WO 96/07617 | 3/1996 |
| GB | 180 668 | 0/1906 | WO | WO 96/15980 | 5/1996 |
| GB | 404 938 | 7/1932 | WO | WO 97/48667 | 12/1997 |
| GB | 406345 | 8/1932 | WO | WO 98/37024 | 8/1998 |
| GB | 467 481 | 9/1935 | WO | WO 99/14208 | 3/1999 |
| GB | 541357 | 11/1941 | WO | WO 99/32397 | 7/1999 |
| GB | 679 536 | 9/1952 | WO | WO 00/24674 | 5/2000 |
| GB | 736641 | 7/1953 | WO | WO 01/41919 | 6/2001 |
| GB | 799 567 | 8/1958 | WO | WO 01/86220 | 11/2001 |
| GB | 1046521 | 1/1964 | WO | WO 02/26672 | 4/2002 |
| GB | 1083594 | 11/1964 | WO | WO 02/059536 | 8/2002 |
| GB | 984446 | 2/1965 | WO | WO 03/064357 | 8/2003 |

| | | |
|---|---|---|
| WO | WO 2004/056758 | 7/2004 |
| WO | wo 2005/021476 | 3/2005 |
| WO | WO 2005/054167 | 6/2005 |
| WO | WO 2005/097722 | 10/2005 |
| WO | WO 2005/115954 | 12/2005 |
| WO | WO 2005/116004 | 12/2005 |
| WO | WO 2006/020234 | 2/2006 |
| WO | WO 2006/100311 | 9/2006 |
| WO | WO 2006/100312 | 9/2006 |
| WO | WO 2006/100313 | 9/2006 |
| WO | WO 2006/100315 | 9/2006 |
| WO | WO 2006/100316 | 9/2006 |
| WO | WO 2006/100317 | 9/2006 |
| WO | WO 2006/100318 | 9/2006 |
| WO | WO 2006/100319 | 9/2006 |
| WO | WO 2006/100320 | 9/2006 |
| WO | WO 20061100314 | 9/2006 |
| WO | WO 2006/106153 | 10/2006 |
| WO | WO 2006/106154 | 10/2006 |
| WO | wo 2006/106155 | 10/2006 |
| WO | WO 2007/005405 | 5/2007 |
| WO | WO 2007/054505 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/026212 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |
| WO | WO 2010/066660 | 6/2010 |

OTHER PUBLICATIONS

Yoshikazu Suzawa et al., Kagachu Sohchi (Chemical Apparatuses), vol. 23, No. 11, 3744 (published on Nov. 1981) with English translation.
Journal of American Oil Chemists' Society Jul. 1982, vol. 59, No. 7 pp. 292-295.
Chemical Engineering Handbook, 6th Revised Edition, 2nd print issued on Apr. 25, 2001, with attached English translation.
Organic synthesis, Part 1, published by Scientific Publishing, 1957.
Handbook of chemical products, organic chemical materials, Second edition, published by Chemical Industry Press, Jan. 1995.
R. A. Kiseleva and V.M. Goncharko, J. Appl. Chem USSR, 1971, vol. 44, pp. 2086-2090.
Handbook of Corrosion data and material selection, published by Chemical Industry Press, edited by Jingyi Zuo, Yu Zuo; first edition, Oct. 1996 with attached English translation.
Handbook of azeotropic mixture, edited by information department of comprehensive scientic technology research institution of Fushun city, 1993.
Industry chemical reaction and application, published by Chinese Scientific Technology University Press, 1999 with attached English translation.
Epoxy resin, published by Shanghai People's Publishing House, 1971, with attached English translation.
Boschan and S. Winstein, Journal of the American Chemical Society, 1956, vol. 78, pp. 4921-4925.
Encyclopedia for Chinese Adult Education, 1994, p. 623.
"Electrolytic cell test for electrolysis of epoxy sewage salt to prepare chlor-alkali", process Equipment Department of Research Institute of chlor-alkali, Shengyang chemical Plant, Liaononhg Chemical Industry, Issue No. 2, pp. 32-37, published Dec. 31, 1981, with attached English translation.
"Analysis of the Composition of the Byproduct During the Manufacturing Process of Sepichlorhydrin by GC-MS", Ren Chengxin et al.,
Chemical Analysis and Measurement, vol. 12, Issue No. 3, p. 25-26, Dec. 31, 2003, with attached English translation.
Encyclopedia of Chemical Technology, vol. 5, Nov. 1993.
Manufacture and use of epoxy resin, edited by Shanghai Resin Factory, published by China Petrochemical Press, First Edition, Oct. 1974.
U.S. Appl. No. 60/560,676, filed Apr. 8, 2004, Gilbeau, et al.
U.S. Appl. No. 60/734,659, filed Nov. 8, 2005, Krafft, et al.
U.S. Appl. No. 60/734,627, filed Nov. 8, 2005, Krafft, et al.
U.S. Appl. No. 60/734,657, filed Nov. 8, 2005, Krafft, et al.
U.S. Appl. No. 60/734,658, filed Nov. 8, 2005, Gilbeau, et al.
U.S. Appl. No. 60/734,635, filed Nov. 8, 2005, Krafft, et al.
U.S. Appl. No. 60/734,634, filed Nov. 8, 2005, Krafft, et al.
U.S. Appl. No. 60/734,637, filed Nov. 8, 2005, Krafft, et al.
U.S. Appl. No. 60/734,636, filed Nov. 8, 2005, Krafft, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Unknown.
U.S. Appl. No. 13/131,516, filed May 26, 2011, Gilbeau, et al.
Gibson., "The Preparation, Properties, and Uses of Glycerol Derivatives, Part III. The Chlorohydrins", Chemistry and Industry, Chemical Society, pp. 949-975, 1931.
Carre et al., "La Transformation des Alcools Polyatomiques en Mono-et en Polychlorhydrines au Moyen du Chlorure de Thionyle", Bull. Soc. Chim. Fr., No. 49, pp. 1150-1154, 1931.
Fauconnier, "Preparation de L'Epichlorhydrine", Bull. Soc. Chim. Fr., No. 50, pp. 212-214, 1888.
"Industrially Important Epoxides", Ullmann's Encyclopedia of Industrial Chemistry, 5.ed, vol. A9, pp. 539-540.
Bonner et al., "The Composition of Constant Boiling Hydrochloric Acid at Pressures of 50 to 1220 Millimeters", Journal of American Chemical Society, vol. 52, pp. 633-635, 1930.
Muskopf et al., "Epoxy Resins", Ullmann's Encyclopedia of Industrial Chemistry, 5.ed, vol. A9, pp. 547-562.
Armando Novelli, "The Preparation of Moni- and Dichlorohydrins of Glycerol," Anal. Farm. Bioquim, vol. 1, 1930, pp. 8-19 (with English Abstract).
Ullmann Encyclopedia Industr. Chem. 5th Ed., vol. A13, (1989) pp. 289.
Ullmann Encyclopedia Industr. Chem. 5th Ed., vol. A11, (1988) pp. 354-360.
Derwent Publications, AN 109:6092 CA, JP 62-242638 (Oct. 23, 1987).
Derwent Publications, AN 1987-338139 [48], JP 62-242638, (Oct. 23, 1987).
Kirk-Othmer Encyclopedia of Chemical Technology, Third Edition, vol. 4, Blood, Coagulants and Anticoagulants to Cardiovascular Agents.
J.B. Conant et al., "Glycerol a,y-Dichlorophydrin," Organic Syntheses Coll., vol. 1, p. 292, 1941.
I. Miyakawa et al., Nagoya Sangyo Kagaku Kenkyusho Kenkyu Hokoku, 10, 49-52 (1957).
Han Xiu-Ying et al., Shanxi Daxue Xueba Bianjibu, 2002, 25(4), 379-80.
The Journal of the American Chemical Society, vol. XLV, Jul.-Dec. 1923, pp. 2771-2771.
Berichte Der Deutschen Chemischen Gesellschaft, 1891, Vo. 24, pp. 508-510.
Perry Chemical Engineers Handbook $7^{th}$ Ed. $11^{th}$ Section (1997).
Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870.
Oleoline, com, Glycerine Market report, Sep. 10, 2003, No. 62.
Notification Under Act No. 100/2001, Coll. as Amended by Act. No. 93/2004, Coll. To the extent of Annex No. 4, (SPOLEK) Nov. 30, 2004.

Documentation Under Act No. 100/2001 Coll. As amended by Act No. 93/2004 Coll in the scope of appendix No. 4 (SPOLEK) Jan. 11, 2005.
K. Weissermel and H J. Arpe in Industrial Organic Chemistry, Third, Completely Revised Edition, VCH, 1997, pp. 149,275.
Industrial Bioproducts: "Today and Tomrrow," Energetics, Inc. for the U.S. Department of Energy, Office of Energy Efficiency and Renewable Energy, Office of the Biomass Program, Jul. 2003, pp. 49, 52 to 56.
Kirk Othemer Encyclopedia of Chemical Technology, Fourth Edition, 1992, vol. 2, p. 156, John Wiley & sons, Inc.
Ullmann's Encyclopedia of Industrial Chemistry, Fifth, Completely Revised Edition, 1985, vol. A13, pp. 292-293.
The Merck Index, Eleventh Edition, 1989, pp. 759-760.
Ullmann's Encyclopedia of Industrial Chemistry, Fifth Completely Revised Edition, vol. A1, pp. 427-429.
Ullmann's Encyclopedia of Industrial Chemistry, Fifth Completely REvised Edition, vol. A6, pp.240-252.
Hancock, E.G., Propylene and its Industrial Derivatives, 1973, pp. 298-332.
K. Weissermel and H. J. Arpe in Industrial Organic Chemistry, Third, Competely Revised Edition, VCH 1997, pp. 149-163.
K. Weissermel and H. J. Arpe in Industrial Organic Chemistry, Third, Completely Revised Edition, VCH 1997, pp. 275-276.
Ullmann's Encyclopedia of Industrial Chemistry, Fifth Completely Revised Edition, vol. A9, pp. 539-540.
Perry's Chemical Engineers Handbook, Sixth Edition, Robert H. Perry, Don Green, 1984, Section 21-44 to 21-68.
Iwanami Dictionary of Physics and Chemistry, Third edition, Ryo Midorikawa/Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll,. as amended by later regulations of the project/intent combined process for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the $6^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.
Product Brouchure of De Dietrich Company, Apr. 1996, pp. 3, 8 and 9 w/English translation of p.8, left column, lines 1-4, p. 9.
Semendyava, N.D. et al., Khimicheskaya Promyshlennost, Seriya: Khornaya Promyshlennost (1981), 5, 21-2 (CA Summary) XP 002465275.
Rudnenko, E.V., et al., Kakokrasochnye Materialy I Ikh Primenenie (1988), 4, 69-71 (CA Summary) XP 002465276.
Herman A. Bruson, et al., "Thermal Decomposition of Glyceryl Carbonates," Journal of the American Chemical Society, vol. 74, Apr. 1952 pp. 2100-2101.
Perry Chemical Engineers Handbook $7^{th}$ Ed. $13^{th}$ Section (1997).
Perry Chemical Engineers Handbook $7^{th}$ Ed. $15^{th}$ Section (1997).
W. Giger et al., "14C/12C-Ratios in Organic Matter and Hydrocarbons Extracted from Dated Lake Sediments," Nuclear Instruments and Methods in Physics Research B5 (1984), 394-397. XP-002631954.
Jurgen O. Metzger, "Fats and Oils as Renewable Feedstock for Chemistry," Eur. J. Lipid Sci. Technol. (2009), 111, 865-876. XP-002631953.
Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.
Bruce M. Bell, "Glycerin as a Renewable Feedstock for Epichlorohydrin Production. The GTE Process," Clean-Soil, Air, Water, vol. 36, No. 8, (2008) pp. 657-661. XP-02631952.
Ullmann Encyclopedia Industr. Chem. $5^{th}$ Ed., vol. A23, (1993) pp. 635-636.
Catalogue of Nittetu Chemical Engineering Ltd. (Published in Mar. 1994).
12093 Chemical, Chemical Daily Co., Ltd. (Published on Jan. 22, 1993) with attached English translation of relevant excerpts.

Chemicals Guide, Chemical Daily Co., Ltd. (Published on Jun. 15, 1990) with attached English translation of relevant excerpts.
Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd. (and similar passages but retrieved from the English $5^{th}$ Edition of the Book, 1987.
Myszkowski J. et al., "Removal of Chlorinated Organic Impurities from Hydrogen Chloride," CA, Jan. 1, 1900, XP002352444 (English CA Summary only).
Myszkowski J. et al., "Removal of Organic Compoiunds from Gaseous Hydrogen Chloride by an Absorption Method," CA, Jan. 1, 1900, XP002352445 (English CA summary only).
Milchert E. et al., "Recovering Hydrogen Chloride and Organic Chlor Compounds from the Reaction Mixture in the Chlorination of Ethylene," CA, Jan. 1, 1900, XP002352443 (English CA summary only).
Laine D.F., et al., "The Destruction of Organic Pollutants Under Mild Reaction Conditions : A Review," Microchemical Journal, vol. 85, No. 2, 2006, pp. 183-193.
Rainwater Harvesting and Utilization, Internet Citation, XP003003726.
H. Galeman, Organic Synthesis, Section 1, pp. 234-235.
Chemical Encyclopedia 5, p. 456.
Epoxy Resins, Shanghai Resin Plant, Shangai People's Press, 1971.
Martinetti Richard et al., "Environment Le Recyclage De l'eau," Industrie Textile, Ste. Sippe Sarl, Metz, FR., No. 1300, Jul. 1, 1998, ISSN: 0019-9176.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V;—2005 p. 81/-8/5., vol. 5.
Klaus Weissermel, et al., "Industrial Organic Chemistry," ($3^{rd}$ Completely Revised Edition); VCH 1997. p.93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997, p. 347-355.
M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.
Medium and Long-Term Opportunities and Risks of the Biotechnological Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).
Ullmann Encyl. Industr. Chem., $5^{th}$ Ed., vol. A6, (1988), pp. 401-477.
Polymer Science Dictionary, M.S.M., Elsevier Applied Chemistry, London and New York 1989, p. 86.
Perry's chemical Engineers' Handbook, Sixth Edition, Section 21, pp. 21-55.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).
Fauconnier, "Preparation of Epichlorohydrin," Bull. Soc. Chim. Fr., No. 122, pp. 212-214 (With English Translation).
Ullmann's Encyclopedia of Industrial Chemistry, 2005, Wiley-VCH GmbH & Co., KgaA, Weinheim, pp. 8-15 and 401-477, Published online Mar. 15, 2001.
RD 436093, Aug. 10, 2000, Research Disclosure.
Ma Zengxin, Gan Yicui, Recovery of Polyglycerol from Residues of Synthetic Glycerol—Riyong Huaxue Gongye, 1997, 4, 21023 (Abstract Only).

Production and Prospect of the World Natural Glycerol by Zhu Shiyong, Cereals and Oils, vol. 1, 1997, pp. 33-38 (No English Translation).
Vinnolit; Vinnolit receives EU grant for water recycling project; Press Release, 2008: http://www.vinnolit.de/vinnolit.nsf/id/EN_Vinnolit_receives_EU_grant_for_water_recycling_project_.
N.W. Ziels, Journal of American Oil Chemists' Society, Nov. 1956, vol. 33, pp. 556-565.
Perry's Chemical Engineers Handbook, Sixth Edition, McGraw Hill Inc., (1984) Section 18.
Vol. B3: Unit Operations II of Ullmann's Encyclopedia of Industrial Chemistry, Fifth Completely Revised Edition, Published by VCH, 1988.
New Experimental Chemical Course 1, Basic Operation I, Section 4, Separation and Purification, pp. 251-252, Issued Sep. 20, 1975 (with English Translation).
Copyright Mar. 1992, Advanced Organic Chemistry, 4$^{th}$ Ed., pp. 889, 908 and 937.
Yong, K.C., et al., "Refining of Crude Glycerine Recovered from Glycerol Residue by Simple Vacuum Distillation," Journal of Oil Palm Research, vol. 13, No. 2, Dec. 2001, pp. 39-44.
Friedel et Silva, Bulletin de la Socieété Chimique de Paris, Année 1873, 1er semestre—Nouvelle Série—Tome XIX, p. 98.
I.S. Neuberg, Biochemische Zeitshrift, 1930, vol. 221, pp. 492-493.
F. Krausz Ann. De Chimie, 12e série, t. 4 Nov.-Dec. 1949, pp. 811-931.
Glycerin : An overview, Soap and Detergent Association. Copyright 1990 by the Soap and Detergent Association.
Chemical and Engineering News, 1948, 26 (38), pp. 2770-2771.
Fairbourn et al., "The Partial Esterification of Polyhydric Alcohols. Part XII. The Function of Ethylene-oxide Rings," J. Chem. Soc. 1932, pp. 1965-1972.
Clarke et al., Organic Syntheses, Coll., vol. 1, p. 233, (1941); vol. 3, p. 47, (1923).
Braun, Organic Syntheses, Coll., vol. 2, p. 256, (1943); vol. 6, p. 30, (1936).
Conant et al. Organic Syntheses, Coll., vol. 1, p. 292, (1941); vol. 2, p. 29, (1922).
Bull. Soc. Chim. Fr. (1943), 10, pp. 52-58, with English Translation.
Schröder et al. "Glycerol as a By-Product of Bioldiesel Production in Diets for Ruminants," Institute of Animal Nutrition, Physiology and Metabolism, University of Kiel, 24098 Kiel, 1995.
"Chemical Properties and Derivatives of Glycerol", (1965), published by Glycerine Producers' Association in New York, pp. 1-20.
G.W. Busby and D.E. Gosvenor, "The Purification of Glycerin by Ion-Exchange," The Journal of The American Oil Chemists' Society, vol. 29, No. 8, pp. 318-320 (1952).
L.L. Lamborn, "Modern Soaps, Candles and Glycerin," D. Van NOstrand Company, London, third edition 1918, pp. 542-550, 573-574.
G. Knothe, "Historical perspectives on vegetable oil-based diesel fuels", Inform. vol. 12, Nov. 2001, pp. 1103-1107.
U. Schuchardt et al., "Transesterification of Vegetable Oils: a Review," J. Braz. Chem. Soc., vol. 9, No. 1, 199-210, 1998.
S. Claude, "Research of new outlets for glycerol—recent developments in France," Fett/Lipid 101 (1999), Nr. 3, S 101-104.
C.B. Prakash, "A critical review of Biodiesel as a Transportation Fuel in Canada," for the Transportation Systems Branch Air Pollution Prevention Directorate Enviornment Canada, Mar. 25, 1998, pp. 1-104.
H. Fukuda et al., "Biodiesel Fuel Production by transesterification of Oils", Journal of Bioscience and Bioengineering, vol. 92, No. 5, pp. 405-416 (2001).
Encyclopedia of Experimental Chemistry I, Basic Operation I, edited by The Chemical Society of Japan, Maruzen Co., Ltd., Nov. 5, 1990, 4th Edition, pp. 161 to 165 and 184 to 191 (no English translation available.
Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312 and 313 (no English translation available).
Clarke et al., Org Synth., Coll. vol. 1, p. 233-234, 1964.
Braun, Org. Synth., Coll., vol. 2, p. 256-259, 1957.
Kirk Othmer Encyclopedia of Chemical Technology, 3rd Edition, vol. 9, pp. 267-289, 1980.

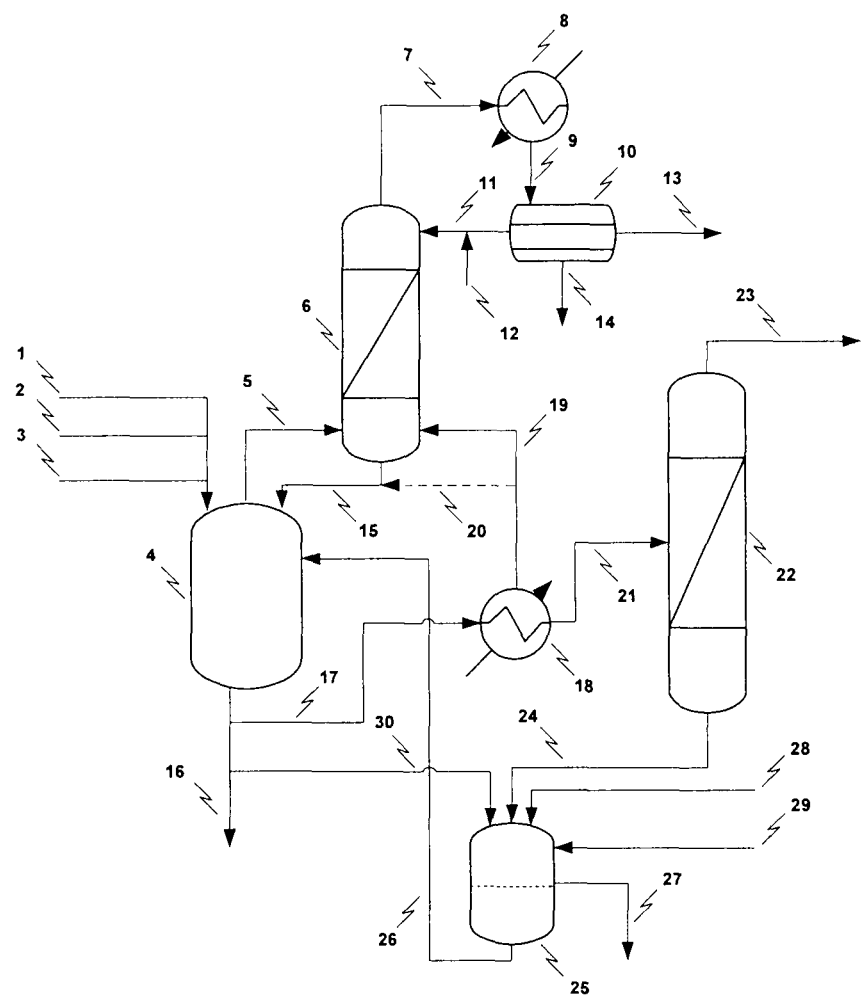

PROCESS FOR PRODUCING AN ORGANIC COMPOUND

The present patent application is a continuation of U.S. application Ser. No. 11/915,059, filed Nov. 20, 2007, now allowed, incorporated herein by reference; which is a 371 of PCT/EP2006/062438 371 filed May 19, 2006. This application also claims benefit of patent application FR 05.05120 and patent application EP 05104321.4, both filed on May 20, 2005 and of U.S. Provisional Patent Applications 60/734,659, 60/734,627, 60/734,657, 60/734,658, 60/734,635, 60/734,634, 60/734,637 and 60/734,636, all filed on Nov. 8, 2005, the contents of which are incorporated herein by reference.

The present invention relates to processes for producing an organic compound, in particular to a process for producing a chlorohydrin.

It is known that natural petrochemical resources, for example oil or natural gas, that are available on earth are limited. Now, these resources are used for producing fuels and as a starting product for producing a large variety of useful organic compounds such as monomers or reactants for producing plastics, for example, ethylene oxide and chloroethanol (see for example K. Weissermel and H.-J. Arpe in Industrial Organic Chemistry, Third Completely Revised Edition, VCH Editor, 1997, page 149), propylene oxide and monochloropropanol (see for example K. Weissermel and H.-J. Arpe in Industrial Organic Chemistry, Third Completely Revised Edition, VCH Editor, 1997, page 275), epichlorohydrin or dichloropropanol (see, for example, Ullmann's Encyclopedia of Industrial Chemistry, 5. ed., Vol. A9, p. 539-540). Documents Chemistry and Industry, Nov. 20, 1931, Part III, pages 949 to 954, and Nov. 27, 1931, Part III, pages 970 to 975, describe a process for the synthesis of dichloropropanol from glycerol and hydrochloric acid in the presence of acetic acid as acid catalyst.

According to known processes for producing chlorohydrins, the product is generally obtained in highly diluted aqueous solution with a titre of 5 to 15% by weight. It is then particularly expensive to purify it. Moreover, in the case of dichloropropanol, the major isomer obtained according to such processes is 2,3-dichloropropane-1-ol.

It was desirable to find uses and processes making it possible to reduce the consumption of natural petrochemical resources, in particular for the abovementioned uses.

It was also desirable to find processes for re-using by-products of other production processes so as to minimize the overall amount of by-products having to be eliminated or destroyed.

It was also desirable to find processes for minimizing the cost of separation operations linked to highly diluted aqueous solutions.

Consequently, the invention relates to a process for producing a chlorohydrin by reaction between a multihydroxylated-aliphatic hydrocarbon, an ester of a multihydroxylated-aliphatic hydrocarbon, or a mixture thereof, and a chlorinating agent, according to which the multihydroxylated-aliphatic hydrocarbon, the ester of a multihydroxylated-aliphatic hydrocarbon, or the mixture thereof used contains at least one solid or dissolved metal salt, the process comprising a separation operation to remove at least part of the metal salt.

The term "multihydroxylated-aliphatic hydrocarbon" refers to a hydrocarbon which contains at least two hydroxyl groups attached to separate saturated carbon atoms. The multihydroxylated-aliphatic hydrocarbon may contain, but not to be limited thereby, from 2 to 60 carbon atoms.

Any single carbon of a multihydroxylated-aliphatic hydrocarbon bearing the hydroxyl (OH) functional group must possess no more than one OH group, and must be sp3 hybridized. The carbon atom bearing the OH group may be primary, secondary or tertiary. The multihydroxylated-aliphatic hydrocarbon used in the present invention must contain at least two sp3 hybridized carbons each bearing an OH group. The multihydroxylated-aliphatic hydrocarbon includes any vicinal-diol (1,2-diol) or triol (1,2,3-triol) containing hydrocarbon including higher orders of contiguous or vicinal repeating units. The definition of multihydroxylated-aliphatic hydrocarbon also includes for example one or more 1,3-, 1,4-, 1,5- and 1,6-diol functional groups as well. The multihydroxylated-aliphatic hydrocarbon may also be a polymer such as polyvinylalcohol. Geminal-diols, for example, would be precluded from this class of multihydroxylated-aliphatic hydrocarbon compounds.

It is to be understood that the multihydroxylated-aliphatic hydrocarbon can contain aromatic moieties or heteroatoms including for example halide, sulfur, phosphorus, nitrogen, oxygen, silicon and boron heteroatoms, and mixtures thereof.

Multihydroxylated-aliphatic hydrocarbons useful in the present invention include for example 1,2-ethanediol (ethylene glycol), 1,2-propanediol (propylene glycol), 1,3-propanediol, 1-chloro-2,3-propanediol (chloropropanediol), 2-chloro-1,3-propanediol (chloropropanediol), 1,4-butanediol, 1,5-pentanediol, cyclohexanediols, 1,2-butanediol, 1,2-cyclohexanedimethanol, le 1,2,3-propanetriol (also known as glycerol, glycerin or glycerine), and mixtures thereof. Preferably, the multihydroxylated-aliphatic hydrocarbons used in the present invention include for example 1,2-ethanediol, 1,2-propanediol, 1,3-propanediol, 1,2,3-propanetriol and mixtures thereof. More preferably, the multihydroxylated-aliphatic hydrocarbons used in the present invention include for example 1,2-ethanediol, 1,2-propanediol, chloropropanediol, 1,2,3-propanetriol and any mixture thereof. 1,2,3-propanetriol is the most preferred.

Esters of multihydroxylated-aliphatic hydrocarbon can be present in the multihydroxylated-aliphatic hydrocarbons and/or can be produced in the process for producing the chlorohydrin according to the invention and/or can be manufactured prior to the process for producing the chlorohydrin. Examples of esters of multihydroxylated-aliphatic hydrocarbon are ethyle glycol mono acetate, propanediol monoacetates, glycerol monoacetates, glycerol monosterates, glycerol diacetates and their mixtures.

The term "chlorohydrins" refers to a compound containing at least one hydroxyl group and at least one chlorine atom attached to separate saturated carbon atoms. A chlorohydrin that contains at least two hydroxyl groups is also a multihydroxylated aliphatic hydrocarbon. Accordingly, the starting material and product of the present invention can each be chlorohydrins. In that case, the product chlorohydrin is more highly chlorinated than the starting chlorohydrin, i.i., has more chlorine atoms and fewer hydroxyl groups than the starting chlorohydrin. Preferred chlorohydrins are for example chloroethanol, chloropropanol, chloropropanediol and dichloropropanol, with dichloropropanol being the most preferred. Particularly preferred chlorohydrins are 2-chloroethanol, 1-chloropropane-2-ol, 2-chloropropane-1-ol, 1-chloropropane-2,3-diol, 2-chloropropane-1,3-diol, 1,3-dichloropropane-2-ol and 2,3-dichloropropane-1-ol and any mixture thereof.

The multihydroxylated-aliphatic hydrocarbon can be a synthetic multihydroxylated-aliphatic hydrocarbon, a multihydroxylated-aliphatic hydrocarbon obtained from renewable raw materials or a mixture thereof. Preferably, the multihydroxylated-aliphatic hydrocarbon used in the process of the invention has at least partially been produced from renewable raw materials. The same considerations apply to the ester of a multihydroxylated-aliphatic hydrocarbon, or the mixture of the ester of a multihydroxylated-aliphatic hydrocarbon and the multihydroxylated-aliphatic hydrocarbon.

The expression « synthetic » means that the multihydroxylated-aliphatic hydrocarbon has been obtained from fossil raw materials. By fossil raw materials, one intends to denote materials derived from natural petrochemical feedstock, like for instance, petroleum, natural gas, and coal. Among those raw materials, organic compounds including 2 and 3 carbon atoms are preferred. When the chlororhydrin is dichloropropanol or chloropropanediol, allyl chloride, allyl alcohol and "synthetic" glycerol are more preferred. By "synthetic" glycerol, one intends to denote a glycerol obtained from petrochemical feedstocks. When the chlorohydrin is chloroethanol, ethylene and "synthetic" ethylene glycol are more preferred. By "synthetic" ethylene glycol, one intends to denote an ethylene glycol obtained from petrochemical feedstocks. When the chlorohydrin is chloropropanol, propylene and "synthetic" propylene glycol are more preferred. By "synthetic" propylene glycol, one intends to denote a propylene glycol obtained from petrochemical feedstocks. The same considerations apply to the ester of a multihydroxylated-aliphatic hydrocarbon, or the mixture of the ester of a multihydroxylated-aliphatic hydrocarbon and the multihydroxylated-aliphatic hydrocarbon.

By renewable raw materials, one intends to denote materials obtained from the treatment of renewable raw materials. Among those materials, natural ethylene glycol, natural propylene glycol and natural glycerol are preferred. "Natural" ethylene glycol, propylene glycol and glycerol can be obtained for instance by thermochemical conversion of sugars derived from biomass treatments as described in "Industrial Bioproducts: Today and Tomorrow, Energetics, Incorporated for the U.S. Department of Energy, Office of Energy Efficiency and Renewable Energy, Office of the Biomass Program, July 2003, pages 49, 52 to 56". One process is for example the catalytic hydrogenolysis of sorbitol obtained by thermochemical conversion of glucose. Another process is for example the catalytic hydrogenolysis of xylitol obtained by hydrogenation of xylose. Xylose can for example be obtained by hydrolysis of hemicellulose contained in corn fibers.

The expression "glycerol obtained from renewable raw materials" or "natural glycerol" is intended to denote in particular glycerol obtained in the course of the production of biodiesel, or else glycerol obtained during conversions of fats or oils of plant or animal origin in general, such as saponification, trans-esterification or hydrolysis reactions.

Among oils usable in the process of the invention, one can quote all current oils, like the corn, sunflower, old or new colza, babassu, copra, cabbage tree, palm oils, of ricinus and cotton, groundnut oils, soya, flax and crambe and all oils resulting for example from the plants of sunflower or colza obtained by genetic modification or hybridization. One can even use worn oils of crackling, varied animal oils, like fish oils, tallow, the lard and even of greases of squaring. Among oils used, one can still indicate the oils partially modified for example by polymerization or oligomerization such as for example "linseed oil stand oils", sunflower and puffed up vegetable oil.

A particularly suitable glycerol can be obtained during the conversion of animal fats. Another particularly suitable glycerol can be obtained during the production of biodiesel. Another yet particularly suitable glycerol can be obtained during the conversion of fats or oils of plant or animal origin, by transesterification in the presence of an heterogeneous catalyst, such as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is used in a fixed-bed configuration. In the process according to the invention, glycerol can be as described in the patent application entitled <<Process for preparing a chlorohydrin by conversion of multi-hydroxylated aliphatic hydrocarbons" filed in the name of SOLVAY SA on the same day as the present application, the contents of which are incorporated herein by reference.

Mention is particularly made of a process for manufacturing a chlorohydrin, wherein a multi-hydroxylated aliphatic hydrocarbon, an ester of a multi-hydroxylated aliphatic hydrocarbon, or a mixture thereof, the total metal content of which expressed as elements is higher than or equal to 0.1 µg/kg and lower than or equal to 1 000 mg/kg, is submitted to a reaction with a chlorinating agent.

In contrast, "synthetic multihydroxylated-aliphatic hydrocarbon" is generally obtained from petrochemical resources. The same considerations apply to the ester of a multihydroxylated-aliphatic hydrocarbon, or the mixture of the ester of a multihydroxylated-aliphatic hydrocarbon and the multihydroxylated-aliphatic hydrocarbon.

In the process according to the invention, the multihydroxylated-aliphatic hydrocarbon used can be a crude multihydroxylated-aliphatic hydrocarbon product or a purified multihydroxylated-aliphatic hydrocarbon product. A "crude" multihydroxylated-aliphatic hydrocarbon product is a multihydroxylated-aliphatic hydrocarbon which has not been submitted to any treatment after its manufacture. A "purified" multihydroxylated-aliphatic hydrocarbon product is a multihydroxylated-aliphatic hydrocarbon which has been submitted to at least one treatment after its manufacture. When the multihydroxylated-aliphatic hydrocarbon is a crude product obtained from renewable raw materials, it can comprise, for example, water in addition to a metal salt. The metal salt is in particular a metal chloride, which is preferably chosen from NaCl and KCl. The metal salt can also be selected from metal sulphates such as sodium sulphate and potassium sulfate. The multihydroxylated-aliphatic hydrocarbon used in the process according to the invention contains at least one solid or dissolved metal salt which is preferably selected from sodium chloride, potassium chloride, sodium sulfate and potassium sulfate. The multihydroxylated-aliphatic hydrocarbon used in the process according to the invention has generally a metal salt content of at least 0.5% by weight, preferably greater than or equal to approximately 1% by weight, more preferably greater than or equal to approximately 2% by weight, most preferably greater than or equal to approximately 3% by weight. The metal salt content is generally of at most 15% by weight, preferably less than or equal to 10% by weight, more preferably less than or equal to approximately 7.5% by weight and most preferably less than or equal to 5% by weight. The same considerations apply to the ester of a multihydroxylated-aliphatic hydrocarbon, or the mixture of the ester of a multihydroxylated-aliphatic hydrocarbon and the multihydroxylated-aliphatic hydrocarbon.

In the process according to the invention, the crude multihydroxylated-aliphatic hydrocarbon product can also contain organic impurities such as carbonyl compounds, in particular aldehydes, fatty acids, salts of fatty acids or esters of fatty acids, such as in particular mono- or polyesters of the multihydroxylated-aliphatic hydrocarbon with fatty acid, optionally in combination with water. When the multihydroxylated-aliphatic hydrocarbon is glycerol, preferred fatty acids are saturated and unsaturated fatty acids containing more than 12 carbon atoms like for instance oleic, linoleic and linolenic acids. Those acids are for instance produced during the conversion of colza oil by saponification, trans-esterification and hydrolysis reactions. Preferred esters of fatty acids are methylic esters.

In the process according to the invention, the crude product generally comprises at most 10% by weight of organic impurities, often 8% by weight of organic impurities. Often, the crude product comprises at most 6% by weight of organic impurities. Preferably, it comprises at most 2% by weight of organic impurities. Most preferably, it comprises at most 1% by weight of organic impurities. The organic impurities typically consist essentially of fatty acids and their derivatives.

The invention then also relates to a process for producing a chlorohydrin according to which a multihydroxylated-aliphatic hydrocarbon, an ester of a multihydroxylated-aliphatic hydrocarbon, or a mixture thereof, containing at most 8% by weight of organic impurities is subjected to a reaction with a chlorinating agent.

It has surprisingly been found that the use of crude product having a high content of organic impurities does not have substantial impact on the reaction underlying the process of the invention. Optional byproducts from the organic impurities can easily be eliminated from the reaction mixture e.g., if applicable, by controlling the purge rate as described in the patent application WO 2005/054167 in the name of SOLVAY SA, the content of which is incorporated herein by reference, from page 17, line 33 to page 18, line 2, from page 24, lines 8 to page 25, line 10.

In the process according to the invention, the crude multihydroxylated-aliphatic hydrocarbon product generally comprises at least 40% by weight of the multihydroxylated-aliphatic hydrocarbon. Often, the crude product comprises at least 50% by weight of the multihydroxylated-aliphatic hydrocarbon. Preferably, it comprises at least 70% by weight of the multihydroxylated-aliphatic hydrocarbon. Often, the crude product comprises at most 99% by weight of the multihydroxylated-aliphatic hydrocarbon. Typically, it comprises at most 95% by weight of the multihydroxylated-aliphatic hydrocarbon.

In the process according to the invention, the crude multihydroxylated-aliphatic hydrocarbon product generally comprises at least 5% by weight of water or, in the absence of other compounds than water and the multihydroxylated-aliphatic hydrocarbon, at least 1% by weight of water. In the process according to the invention, the crude multihydroxylated-aliphatic hydrocarbon product generally comprises at most 50% by weight of water or, in the absence of other compounds other than water and the multihydroxylated-aliphatic hydrocarbon, at most 60% by weight of water. Often, the crude multihydroxylated-aliphatic hydrocarbon product comprises at most 30% by weight of water, preferably at most 21% by weight of water.

In another embodiment, the crude multihydroxylated-aliphatic hydrocarbon product comprises at most 89% by weight of the multihydroxylated-aliphatic hydrocarbon. In that embodiment, the crude multihydroxylated-aliphatic hydrocarbon product comprises at most 85% by weight of the multihydroxylated-aliphatic hydrocarbon. In that embodiment, the crude multihydroxylated-aliphatic hydrocarbon product comprises generally at least 10% by weight of water and often at least 14% by weight of water.

The crude multihydroxylated-aliphatic hydrocarbon product has a metal salt content of at least 0.5% by weight, preferably greater than or equal to approximately 1% by weight and more preferably greater than or equal to approximately 1.5% by weight. The crude multihydroxylated-aliphatic hydrocarbon has a metal salt content of at most 15% by weight, preferably less than or equal to 12% by weight and more preferably less than or equal to approximately 7.5% by weight.

The separation operation according to the invention applies particularly preferably to the production of chlorinated compounds starting from a multihydroxylated-aliphatic hydrocarbon, especially to the production of chlorohydrins and epoxides. Surprisingly, the separation operation according to the invention makes it possible to economically obtain these compounds starting from renewable resources.

The term « epoxide » is used to describe a compound containing at least one oxygen bridge on a carbon-carbon bond. Generally, the carbon atoms of the carbon-carbon bond are contiguous and the compound can include other atoms than carbon and oxygen atoms, like hydrogen and halogens, for example. Preferred epoxides are ethylene oxide, propylene oxide, glycidol and epichlorohydrin.

Consequently, the invention also relates in particular to a process for producing a chlorinated organic compound, according to which a multihydroxylated-aliphatic hydrocarbon, an ester of a multihydroxylated-aliphatic hydrocarbon, or a mixture thereof, obtained from renewable raw materials is used, and the multihydroxylated-aliphatic hydrocarbon, the ester of a multihydroxylated-aliphatic hydrocarbon, or the mixture thereof, used contains at least one solid or dissolved metal salt and the process comprises a separation operation to remove at least part of the metal salt. It is understood that the methods of production described hereinafter can also be carried out with multihydroxylated-aliphatic hydrocarbons, esters of a multihydroxylated-aliphatic hydrocarbon, or mixtures of esters of a multihydroxylated-aliphatic hydrocarbon and multihydroxylated-aliphatic hydrocarbons in general and are not limited to the preferred use of a multihydroxylated-aliphatic hydrocarbon, esters of a multihydroxylated-aliphatic hydrocarbon, or mixtures thereof obtained from renewable raw materials.

In the following, the expression "chlorinated compound" has to be understood as "chlorohydrin". Preferred chlorohydrins are for example chloroethanol, chloropropanol, chloropropanediol and dichloropropanol, with dichloropropanol being the most preferred.

The term "chloroethanol" is intended to mean a mixture comprising 2-chloroethanol.

The term "chloropropanol" is intended to mean a mixture of isomers comprising 1-chloropropane-2-ol and 2-chloropropane-1-ol.

The term "chloropropanediol" is intended to mean a mixture of isomers comprising 1-chloropropane-2,3-diol and 2-chloropropane-1,3-diol.

The term "dichloropropanol" is intended to mean a mixture of isomers comprising 1,3-dichloropropane-2-ol and 2,3-dichloro-propane-1-ol.

In the process for producing a chlorohydrin according to the invention, the chlorinating agent can be hydrogen chloride and/or hydrochloric acidic as disclosed in the patent application WO 2005/054167 of SOLVAY SA, from page 4, line 30 to page 6, line 2. Mention can particularly be made a chlorinating agent which can be gaseous hydrogen chloride, aqueous solution of hydrogen chloride or combination of both. Hydrogen chloride can arise from a pyrolysis process of chlorinated organic compounds as for example, a production of vinyl chloride, a production of 4,4-methylenediphenyl diisocyanate (MDI) or toluene diisocyanate, or from processes for cleansing metals or by reaction of inorganic acids such as sulphuric acid or phosphoric acid on metal chlorides such as sodium chloride, potassium chloride or calcium chloride.

In the process for producing a chlorohydrin according to the invention, the chlorinated agent can be aqueous hydrogen chloride or hydrogen chloride preferentially anhydrous, arising from an installation for producing allyl chloride and/or an installation for producing chloromethanes and/or an installation of chlorinolysis and/or a high temperature oxidation installation as described in patent application entitled « Process for manufacturing a chlorohydrin by reaction between a multi-hydroxylated aliphatic hydrocarbon and a chlorinating agent" filed in the name of SOLVAY SA on the same day as the present application, the content of which is incorporated herein by reference.

Mention is particularly made of a process for manufacturing a chlorhydrin from a multi-hydroxylated aliphatic hydrocarbon, an ester of a multi-hydroxylated aliphatic hydrocarbon, or a mixture thereof, and a chlorinating agent, this agent containing at least one of the following compounds: nitrogen, oxygen, hydrogen, chlorine, a hydrocarbon, a halogenated organic compound, an oxygenated organic compound and a metal.

Mention is particularly made of a hydrocarbon selected from aromatic hydrocarbons, saturated and unsaturated aliphatic hydrocarbons, or mixtures thereof.

Mention is particularly made of an aliphatic unsaturated hydrocarbon selected from acetylene, ethylene, propylene, butene, propadiene, methylacetylene, and mixtures thereof, of a saturated hydrocarbon selected from methane, ethane, propane, butane and mixture thereof, and of an aromatic hydrocarbon which is benzene.

Mention is particularly made of a halogenated organic compound which is a chlorinated organic compound selected from chloromethanes, chloroethanes, chloropropanes, lchlorobutanes, vinyl chloride, vinylidene chloride, monochloropropenes, le perchloroethylene, trichlorethylene, chlorobutadiene, lchlorobenzenes and mixture thereof.

Mention is particularly made of a halogenated organic compound which is a fluorinated organic compound selected from fluoromethanes, fluoroethanes, vinyl fluoride, vinylidene fluoride and mixtures thereof.

Mention is particularly made an oxygenated organic compound which is selected from alcohols, chloroalcohols, chlorethers and mixtures thereof.

Mention is particularly made of a metal selected from alkaline metals, alkaline-earth metals, iron, nickel, copper, lead, arsenic, cobalt, titanium, cadmium, antimony, mercury, zinc, selenium, aluminium, bismuth and mixtures thereof.

Mention is more particularly made of a process in which the chlorinating agent est issued at least partially from a process for manufacturing allyl chloride and/or from a process for manufacturing chloormethanes and/or from a chlorinolysis process and/or from a process for oxidizing chlorinated compounds at a temperature higher than or equal to 800° C.

In a more preferred embodiment, the chlorinating agent does not contain gaseous hydrogen chloride.

The process for producing a chlorohydrin according to the invention can be carried out in a reactor as specifically disclosed in the patent application WO 2005/054167 of SOLVAY SA from page 6, lines 3 to 23.

Mention is particularly made of an installation made of, or coated with, materials resisting to chlorinating agents, in particular to hydrogen chloride, under the reaction conditions. Mention is more particularly made of an installation made of enamelled-steel or of tantalum.

The process for producing a chlorohydrin according to the invention can be carried out in equipments, made of or coated with, materials that are resistant to chlorinating agents, as described in patent application entitled <<Process for manufacturing a chlorohydrin in equipments resisting to corrosion" filed under the name of SOLVAY SA on the same day of the present application, the content of which is herein incorporated by reference.

Mention is particularly made of a process for manufacturing a chlorhydrin comprising a stage in which a multi-hydroxylated aliphatic hydrocarbon, an ester of a multi-hydroxylated aliphatic hydrocarbon, or a mixture thereof, is submitted to a reaction with a chlorinating agent containing hydrogen chloride and at least one other stage carried out in an equipment, made of or covered with, materials resisting to the chlorinating agent under the conditions of theis stage. Mention is more particularly made of metallic materials such as enamelled-steel, gold and tantalum and of non-metallic materials such as high density polyethylene, polypropylene, poly(vinylidene fluoride), polytetrafluoroethylene, perfluoro alkoxyalcanes and poly(perfluoropropylvinylether), polysulfones and polysulfides, graphite et impregnated graphite.

The process for producing a chlorohydrin according to the invention can be carried out in a reaction mixture as described in patent application entitled « Continuous process for the manufacture of chlorohydrins" filed under the name of SOLVAY SA on the same day as the present application, the content of which is herein incorporated by reference.

Mention is particularly made of a continuous process for manufacturing a chlorhydrin, wherein a multi-hydroxylated aliphatic hydrocarbon, an ester of a multi-hydroxylated aliphatic hydrocarbon, or a mixture thereof, is submitted to a reaction with a chlorinating agent and an organic acid in a liquid reaction medium which composition at the stationnary state comprises the multi-hydroxylated aliphatic hydrocarbon and esters of the multi-hydroxylated aliphatic hydrocarbon, the sum of the contents of the multi-hydroxylated aliphatic hydrocarbon and esters of the multi-hydroxylated aliphatic hydrocarbon being higher than or equel to 1.1 mol % and lower than or equal to 30 mol %, the percentage being expressed with respect to the organic part of the liquid reaction medium.

The organic part of the liquid reaction medium is defined as the sum of the organic compounds of the liquid reaction medium that is to say compounds which molecule contents at least one carbon atom.

In the process for producing a chlorohydrin according to the invention, the reaction between the multihydroxylated-aliphatic hydrocarbon, the ester of a multihydroxylated-aliphatic hydrocarbon, or the mixture thereof, and the chlorinating agent can be carried out in the presence of a catalyst, as specifically disclosed in the patent application WO 2005/054167 of SOLVAY SA from page 6, line 28 to page 8, line 5. Mention is particularly made of a catalyst which is a carboxylic acid or a carboxylic acid derivative having an atmospheric boiling point of greater than or equal to 200° C., preferably adipic acid or an adipic acid derivative.

In the process for producing a chlorohydrin according to the invention, the reaction between multihydroxylated-aliphatic hydrocarbon, the ester of a multihydroxylated-aliphatic hydrocarbon, or the mixture thereof and the chlorinating agent can be carried out at a temperature, a pressure and a residence time as specifically disclosed in the patent application WO 2005/054167 of SOLVAY SA from page 8, line 6 to page 10, line 10.

Mention is particularly made of a temperature of at least 20° C. and at most 160° C., of a pressure of at least 0.3 bar and at most 100 bar, and of a residence time of at least 1 h and at most 50 h.

In the process for producing a chlorohydrin according to the invention, the reaction between the multihydroxylated-aliphatic hydrocarbon, the ester of a multihydroxylated-aliphatic hydrocarbon, or the mixture thereof, and the chlorinating agent can be carried out in a solvent as specifically disclosed in the patent application WO 2005/054167 of SOLVAY SA from page 11, line 12 to 36.

Mention is particularly made of an organic solvent such as a chlorinated organic solvent, an alcohol, a ketone, an ester or an ether, a non-aqueous solvent not miscible with the multihydroxylated aliphatic hydrocarbon such as chloroethanol, chloropropanol, chlorpropanediol, dichloropropanol, dioxane, phenol, cresol and mixtures of chloropropanediol and dichloropropanol, or havy products from the reaction such as oligomers of the multi-hydroxylated aliphatic hydrocarbon at least partially chlorinated and/or esterified.

In the process for producing a chlorohydrin according to the invention, the reaction between the multihydroxylated-aliphatic hydrocarbon, the ester of a multihydroxylated-aliphatic hydrocarbon, or the mixture thereof, and the chlorinating agent can be carried out in the presence of a liquid phase comprising heavy compounds as described in patent application entitled « Process for manufacturing a chlorohydrin in a liquid phase" filed under the name of SOLVAY SA on the same day as the present application, the content of which is herein incorporated by reference.

Mention is particularly made of a process for manufacturing a chlorhydrin in which a multi-hydroxylated aliphatic hydrocarbon, an ester of a multi-hydroxylated aliphatic hydrocarbon, or a mixture thereof, is submitted to a reaction with a chlorinating agent, in the presence of a liquid phase comprising heavy compounds which boiling temperature under 1 bar of absolute pressure is at least 15° C. higher than the boiling point of the chlorohydrin under 1 bar of absolute pressure.

The process for producing a chlorohydrin according to the invention can be carried under batch mode or continuous mode. Continuous mode is preferred.

In the process for producing a chlorohydrin according to the invention, the reaction between the multihydroxylated-aliphatic hydrocarbon, the ester of a multihydroxylated-aliphatic hydrocarbon, or the mixture thereof, and the chlorinating agent is preferably carried out in a liquid reaction medium. The liquid reaction medium can be mono- or multiphases.

The liquid reaction medium is made up of all of the dissolved or dispersed solid compounds, dissolved or dispersed gas, dissolved or dispersed liquids, at the temperature of the reaction.

The reaction medium comprises the reactants, the catalyst, the solvent, the impurities present in the reactants, in the catalyst and in the solvent, the intermediates, the products and the by products of the reaction.

By reactants, one intends to denote the multihydroxylated-aliphatic hydrocarbon, the ester of a multihydroxylated aliphatic hydrocarbon and the chlorinating agent.

Among the impurities present in the multihydroxylated-aliphatic hydrocarbon, one can mention carboxylic acids, carboxylic acid salts, esters of fatty acids with the multihydroxylated-aliphatic hydrocarbon, esters of fatty acids with alcohols used during trans-esterification, inorganic salts such as for example, alkaline and alkaline-earth chlorides and sulfates.

When the multihydroxylated-aliphatic hydrocarbon is glycerol, one can mention among the impurities of glycerol, carboxylic acids, carboxylic acid salts, fatty acid esters such as mono-, di- and triglycerides, esters of fatty acids with alcohols used during trans-esterification, inorganic salts such as for example, alkaline and alkaline-earth chlorides and sulfates.

Among intermediates, one can mention monochlorohydrins of the multihydroxylated-aliphatic hydrocarbon, their esters and/or polyesters, esters and/or polyesters of the multihydroxylated-aliphatic hydrocarbon and esters of polychlorohydrins.

When the chlorohydrin is dichloropropanol, one can mention among intermediates, the monochlorohydrin of glycerol and its esters and/or polyesters, esters and/or polyesters of glycerol and esters of dichloropropanol.

The ester of multihydroxylated aliphatic hydrocarbon can then be a reactant, an impurity of the multihydroxylated aliphatic hydrocarbon or an intermediate.

By products, one intends to denote the chlorohydrin and water. Water can be the water produced by the chlorination reaction and/or water introduced in the process.

Among by-products, one can mention for example, oligomers of the multihydroxylated-aliphatic hydrocarbon, partially chlorinated and/or esterified.

When the multihydroxylated-aliphatic hydrocarbon is glycerol, among by-products, one can mention, glycerol oligomers, partially chlorinated and/or esterified.

Intermediates and by-products can be formed in the various steps of the process, for example, during the manufacture of the chlorohydrin or during the separation steps of the chlorohydrin.

The liquid reaction medium can then contain the multihydroxylated-aliphatic hydrocarbon, the chlorination agent dissolved or dispersed in the form of bubbles, the catalyst, the solvent, the impurities present in the reactant, the catalyst and the solvent, such as salts dissolved or solid for instance, intermediates, products and by-products of the reaction.

In the process according to the invention, the separation of the chlorohydrin from the other compounds of the reaction medium can be carried out as disclosed in the patent application WO 2005/054167 of SOLVAY SA from page 12, line 1 to page 16, line 35 and at page 18, lines 6 to 13. These other compounds are those already mentioned and comprise non-consumed reactants, impurities present in the reactants, in the catalyst and in the solvent, the catalyst, the solvent, the intermediates, water and the by-products of the reaction.

In the process according to the invention, separation and treatment of the other compounds of the reaction medium can be carried out as described in the patent application WO 2005/054167 of SOLVAY SA from page 18, lines 6 to 13.

Mention is particularly made of a separation by azeotropic distillation of a water/chlorhydrin/chlorinating agent mixture in conditions minimizing losses of the chlorinating agent followed by a separation of the chlorohydrin by decantation.

In the process for manufacturing the chlorhydrin according to the invention, the separation of the chlorhydrin from the other compounds of the reaction medium can be carried out as described in the patent application entitled « Process for manufacturing a chlorohydrin » filed under the name of SOLVAY SA, on the same day as the present application, and the content of which is herein incorporated by reference.

Mention is particularly made of a process for manufacturing a chlorhydrin comprising the following steps: (a) a multi-hydroxylated aliphatic hydrocarbon, an ester of a multi-hydroxylated aliphatic hydrocarbon, or a mixture thereof, is submitted to a reaction with a chlorinating agent and an organic acid in order to obtain a mixture containing the chlorhydrin and esters of the chlorhydrin, (b) at least a part of the mixture obtained in step (a) is submitted to one or more treatments in steps subsequent to step (a) and (c) the multi-hydroxylated aliphatic hydrocarbon is added to at least one of the steps subsequent to step (a), so that to react at a temperature of at least 20° C., with the chlorhydrin esters in order to form at least partially esters of the multi-hydroxylated aliphatic hydrocarbon. Mention is more particularly made of a process in which the multi-hydroxylated aliphatic hydrocarbon is glycerol and the chlorhydrin is dichloropropanol.

In the process for manufacturing the chlorhydrin according to the invention, the separation of the chlorhydrin from the other compounds of the reaction medium can be carried out as described in the patent application entitled « Process for manufacturing a chlorhydrin from a multi-hydroxylated aliphatic hydrocarbon" filed in the name of SOLVAY SA on the same day as the present application, and the content of which is herein incorporated by reference.

Mention is particularly made of a process for manufacturing chlorhydrin by reaction between a multi-hydroxylated aliphatic hydrocarbon, an ester of a multi-hydroxylated aliphatic hydrocarbon, or a mixture thereof, and a chlorinating agent in a reactor which is fed with one or more liquid flows containing less than 50% by weight of the multi-hydroxylated aliphatic hydrocarbon, the ester of a multi-hydroxylated aliphatic hydrocarbon, or the mixture thereof, with respect to the weight of the totality of the liquid flows introduced in the reactor. Mention is more particularly made of a process comprising the following steps: (a) a multi-hydroxylated aliphatic hydrocarbon, an ester of a multi-hydroxylated aliphatic hydrocarbon, or a mixture thereof, is reacted with a chlorinating agent in order to obtain at least one medium containing the chlorhydrin, water and the chlorination agent, (b) at least one fraction of the medium obtained in step (a) is withdrawn and (c) the fraction withdrawn at step (b) is submitted to a distillation and/or a stripping operation in which multi-hydroxylated aliphatic hydrocarbon is added in order to separate from the fraction withdrawn at step (b) a mixture containing water and the chlorhydrin exhibiting a chlorinating agent reduced content compared to the chlorinated agent content in the fraction withdrawn at step (b).

In the process for manufacturing the chlorhydrin according to the invention, the separation of the chlorhydrin from the other compounds of the reaction medium can be carried out as described in the patent application entitled « Process for converting multi-hydroxylated aliphatic hydrocarbons into chlrohydrins" filed under the name of SOLVAY SA, on the same day of the present application and the content of which is herein incorporated by reference.

Mention is particularly made of a process for manufacturing a chlorhydrin comprising the following steps: (a) a multi-hydroxylated aliphatic hydrocarbon, an ester of a multi-hydroxylated aliphatic hydrocarbon, or a mixture thereof, is reacted with a chlorinating agent in order to obtain a mixture containing chlorhydrin, chlorohydrin esters and water, (b) at least one fraction of the mixture obtained in step (a) is submitted to a distillation and/or stripping treatment in order to obtain a part concentrated in water, chlorohydrin and chlorhydrin esters, and (c) at least one fraction of the part obtained in step (b) is submitted to a separation operation in the presence of at least one additive so as to obtain a portion concentrated in chlorhydrin and chlorhydrin esters, and which contains less than 40% by weight of water. The separation operation is more particularly a decantation.

In the process according to the invention, separation and treatment of the other compounds of the reaction medium can be carried out as described in the patent application entitled <<Process for manufacturing a chlorhydrin by chlorination of a multi-hydroxylated aliphatic hydrocarbon" filed in the name of SOLVAY SA on the same day as the present application, the content of which is incorporated herein by reference. A preferred treatment can consist of submitting a fraction of the other products to a high temperature oxidation.

Mention is particularly made of a process for manufacturing a chlorhydrin comprising the following steps: (a) a multi-hydroxylated aliphatic hydrocarbon, an ester of a multi-hydroxylated aliphatic hydrocarbon, or a mixture thereof, the alkaline and/or alkaline-earth metals content of which is lower than or equal to 5 g/kg, is reacted with a chlorinating agent and an organic acid, so as to obtain a mixture containing at least the chlorohydrin and by-products, (b) at least one part of the mixture obtained at step (a) is submitted to one or more treatments in steps subsequent to step (a) and (c) at least one step subsequent to step (a) is an oxidation at a temperature higher than or equal to 800° C. Mention is more particularly made of a process in which in the subsequent step, a part of the mixture obtained at step (a) is withdrawn and that part is submitted to an oxidation at a temperature higher than or equal to 800° C., during the withdrawal. Mention is also made of a process in which the treatment of step (b) is a separation operation selected from the operations of decantation, filtration, centrifugation, extraction, washing, evaporation, stripping, distillation, adsorption or the combination of at least two of them.

In the process for producing a chlorhydrin according to the invention, vapour stripping, in particular steam stripping of the reaction medium, can be carried out. The reaction medium is defined as above. This medium is preferably a liquid reaction medium (a liquid phase) as defined above. When the reaction medium is a liquid phase, the expression "reaction medium" also includes the gas phase in equilibrium with the liquid. In the following, the expression "reaction medium" will then be used to designate indistinctly the liquid phase where the reaction between the multihydroxylated-aliphatic hydrocarbon and the chlorinating agent occurs and the gas phase in equilibrium with that liquid phase. When vapour stripping of the reaction medium is carried out, it is possible to obtain a stripped fraction containing from 1 to 5, some times from 2 to 3 and preferably from 1.5 to 2.5 mol/l of chlorinated organic compound, in particular of chlorohydrin. The stripped fraction is mainly composed of water and the chlorohydrin.

In the process for producing a chlorhydrin according to the invention, when the chlorhydrin is not completely removed from the reaction mixture by withdrawal of a fraction containing water, it is possible to recover at least another fraction of the reaction mixture containing the chlorhydrin.

In this aspect of the process for producing a chlorhydrin according to the invention, at least one fraction comprising from 50 to 95% by weight of the chlorohydrin and at most 50% by weight of water is generally recovered. Preferably, this fraction comprises from 75 to 99.9%, often from 75 to 99%, by weight of the chlorohydrin and from 0.01 to 25%, often from 1 to 25%, by weight of water.

The recovery is preferably carried out by distillation or evaporation. Other fractions obtained during this step, comprising, for example, intermediates and, optionally, the multihydroxylated-aliphatic hydrocarbon and the catalyst, can be recycled to the reaction with the chlorinating agent. It is also possible to separate at least one fraction containing heavy by-products of the reaction, such as described in the patent application WO 2005/054167 of SOLVAY SA from page 11, line 32 to page 11, line 34, in particular chlorinated polymers of the multihydroxylated-aliphatic hydrocarbon, which can be destroyed or can optionally be used in a process for producing polymers of the multihydroxylated-aliphatic hydrocarbon, for example by dechlorination.

The distillation or evaporation is generally carried out at a temperature of at least 20° C. This temperature is often at least 60° C. It is preferably at least 70° C. The distillation or evaporation is generally carried out a temperature of at most 180° C. This temperature is preferably at most 140° C.

The distillation or evaporation is generally carried out at a pressure of greater than 0.001 bar. This pressure is preferably greater than or equal to approximately 0.003 bar. The distillation or evaporation is generally carried out at a pressure of at most 15 bar. This pressure is often at most 10 bar. It is preferably at most 7 bar, more preferably at most 1 bar, yet more preferably at most 0.5 bar and most preferably at most 0.1 bar.

The distillation or evaporation operation can be carried out either by means of distillation columns or by means of evaporators, of film evaporators or alternatively of wiped thin film evaporators.

The recoverable fractions of the residues can be separated there from by physical and/or chemical operations. An example of physical operation is a distillation advantageously by means of a wiped thin film evaporator with an interior or exterior condenser. An example of a chemical operation is an hydrolysis of the residue to recover for instance the catalyst.

In a particular variant of the process of the invention, when the chlorohydrin is a dichlorohydrin, the dichlorohydrin is produced according to a process comprising:
(a) a first reaction step in which a multihydroxylated-aliphatic hydrocarbon is brought into contact with the chlorinating agent so as to obtain a fraction of products comprising at least a monochlorohydrin;
(b) optionally at least part of the fraction of products is subjected to a drying operation;
(c) at least part of the fraction of optionally dried products is introduced into a second reaction step in which at least part of the monochlorohydrin is reacted with the chlorinating agent.

Steps (a) and (c) in this variant are preferably carried out under conditions and with the preferences as described above for the process for producing the chlorohydrin according to the invention. However, it is preferred to carry out the reaction of step (a) in the presence of water at a concentration preferably ranging from 3 to 40% by weight, preferably from 3 to 40% by weight relative to the total weight of the reaction medium.

Step (b) can be carried out, for example, by a stripping operation in at least one of the reactors of steps (a) or (c) or by means of an evaporator placed on a recirculation pipe exterior to the reactor or by distillation. According to another preferred variant, the water is removed by means of a membrane technique.

The process for producing a chlorohydrin according to the invention can be carried out, for example, in cascade reactors, in at least one plate column or in at least one bubble column, or an assembly of such reactors.

The reactors may effectively be of a type that is stirred either by means of internal stirring, or by means of a recirculation pipe exterior to the reactor.

When, in the process according to the invention, the reaction medium is heated, the heating can be obtained, for example, by means of a jacket or by means of an internal heat exchanger. Heating can also be obtained by means of a heat exchanger on a recirculation pipe exterior to the reactor. Optionally, the heating is obtained by combined use of a jacket and of a heat exchanger on a recirculation pipe exterior to the reactor.

In particular when the process according to the invention is operated in a continuous or fed-batch mode, secondary reactions can lead to the build-up in the reactor of by-products of low volatility, among which more or less chlorinated oligomers of the multihydroxylated-aliphatic hydrocarbon. This build-up can lead to a progressive increase of the volume of the reaction medium, to a progressive loss of productivity and require a continuous or discontinuous purge of the reactor to keep the volume at an adequate level. By the expression "purge", one intends to denote a withdrawal of a fraction of the reaction medium.

If appropriate, the catalyst quantity which is removed during such purging operation can be compensated by the introduction of an equivalent quantity of pure or purified catalyst.

The catalyst contained in the purge from the reaction mixture can be economically recycled in the reactor after a purification treatment. For example, catalysts with low solubility in water can be subjected to an acid hydrolysis treatment, preferably carried out at a temperature higher than 30° C., preferably at least 50° C. which is followed by a separation step e.g. by decantation, filtration or extraction. It has been found that in the case of adipic acid, an acid hydrolysis of the purge leads after cooling and filtration, to the recovery of crystallised adipic acid of high purity with a good yield.

In particular when the process according to the invention is operated in a continuous or fed-batch mode, metal salts, in particular NaCl, optionally present in the raw materials, for example in the multihydroxylated-aliphatic hydrocarbon, the ester of a multihydroxylated-aliphatic hydrocarbon, or the mixture thereof, from renewable resources described above, can concentrate in the reactor where the reaction between the multihydroxylated-aliphatic hydrocarbon, the ester of a multihydroxylated-aliphatic hydrocarbon, or the mixture thereof, and the chlorinating agent is carried out. An increase of metal salt content could possibly lead to a progressive crystallisation of insoluble materials, leading to an increase of the volume of the reaction mixture and to various problems linked to the presence of solid materials such as deposit formation on the reactor walls, on the stirrer and on feed and purge lines and valves. Deposit formation on the reactor wall can reduce the heat transfer efficiency and require an increase amount of energy to maintain the temperature of the reaction mixture. Deposit formation on valves and lines can lead to plugging problems. An increased amount of solid in the reaction mixture can reduce the stirring efficiency and require a higher amount of energy to reach a correct agitation. Increase of metal salt concentration could then require a higher continuous or discontinuous purge rate leading to higher losses of products.

While the presence of metal salt is surprisingly acceptable in the process according to the invention, it may therefore be desirable to remove at least part of the metal salt, in particular NaCl, from the reaction system, e.g. in order to prevent optional accumulation of metal salt in the reaction mixture. Such removal can suitably be carried out by subjecting at least a fraction of the reaction mixture which contains metal salt, solid or dissolved, to a treatment comprising at least one separation operation to remove at least part of the metal salt from said fraction.

The separation operation can be selected from liquid/solid, liquid/liquid, liquid/gas and solid/gas separations.

The liquid/solid separation operation can be selected from decantation, centrifugation, filtration, adsorption and treatment with ion-exchanged resins. The liquid/liquid separation operation can be selected from decantation and centrifugation. The liquid/gas separation operation can be selected from stripping, evaporation and distillation.

Liquid/solid separation operations are preferred, filtration is more preferred and filtration where the metal is removed as a solid is most preferred.

In the process according to the invention, the reaction is preferably carried out in a reaction mixture and the separation operation is carried out on at least a fraction of the reaction mixture. The fraction of the reaction mixture can be submitted to a treatment to remove at least one component other than the metal salt prior to the separation operation. That treatment can be a stripping or a distillation operation;

The fraction of the reaction mixture to be submitted to the separation operation can be directly withdrawn from the reaction mixture, notably when the reaction is carried out in the liquid phase. The fraction of the reaction mixture to be submitted to the separation operation can also be withdrawn from the reaction mixture and further treated before removing the metal salt. An example of a suitable treatment is a concentration operation carried out on a liquid fraction of the reaction mixture wherein volatile compounds such as starting materials and products of the reaction, which may optionally be recovered and/or recycled to the reaction mixture, are separated e.g. by stripping, distillation or evaporation and a concentrated fraction having increased content of metal salt, solid or dissolved, is obtained and subjected to the treatment to separate metal salt.

The separation step can then be carried out at any step of the process for producing the chlorohydrin as described in the patent application WO 2005/054167 of SOLVAY SA from page 12, line 1 to page 18, line 13, for instance after the chlorination reaction, after the step of removing a mixture of the chlorhydrin and water from the reaction mixture, after the recovery of chlorohydrin by distillation or evaporation, after the purge of by-products of reaction or after the treatment for recovering the catalyst from the purge.

In a preferred embodiment, the fraction of the reaction mixture which contains metal salt is obtained from the purge of the reactor where the reaction takes place and is sent to a least one separation unit, where the separation of the metal salt is carried out for example by adsorption, distillation, extraction, decantation, centrifugation, filtration and treatment with ion exchanged resins. A liquid/solid separation unit is preferred and a separation by filtration is more preferred. The separated liquid is preferably recycled back to the reactor and the metal salt is left on the filter.

The filtration step can be carried out at a temperature which is usually greater than or equal to 4° C., preferably greater than or equal to 20° C., more preferably greater than or equal to 30° C., yet more preferably greater than or equal to 50° C. and most preferably greater than or equal to 80° C. This temperature is generally lower than or equal to 150° C. and preferably lower than or equal to 140° C.

The nature of the filtration system is not critical and is readily apparent to the skilled person aware of the present invention. A description of suitable filtration systems can be found in "Perry's Chemical Engineers' Handbook, Sixth Edition, 1984, Sections 19-65 to 19-103".

As the metal salt accumulates on the filtration system, it is generally recommended to periodically regenerate the filtration unit by removing the filtrated salt. The regeneration can be performed by any means, for example by removing, in particular by mechanical means, the solid or by dissolving the solid. Optionally, solid elution treatments can be incorporated in the regeneration procedure.

In a one embodiment according to the invention, the metal salt is removed as a solid from the filtration system without any pretreatment.

In a first variant, the salt is disposed off in a suitable manner without further treatment.

In a second variant, the salt is stored in a separate vessel for further treatment. Further treatment can include elution of the solid with solvents and dissolution of the solid with solvents. Such treatments are described herebelow in the preferred embodiment.

In a preferred embodiment according to the invention, the metal salt is treated before removal from the filtration system.

Optionally adsorbed products and reactants such as in particular catalyst and chlorohydrins and their esters can be recovered from the metal salts, in particular from NaCl, for example by elution with an appropriate eluting solvent such as a mixture of water and the chlorohydrin. Any ratio between water and the chlorohydrin is suitable. It is preferred to use the chlorohydrin saturated with water at room temperature. It is particularly preferred to use one of the phase obtained from the decantation between the chlorohydrin and water. The water content of the chlorohydrin used as eluting solvent is generally lower than or equal to 20% by weight and preferably lower than or equal to 15% and most preferably lower than or equal to about 12%. The water content in the mixture of water and the chlorohydrin is generally higher than or equal to 1% by weight.

In another embodiment, the eluting solvent consists essentially of the chlorohydrin. In this embodiment, the water content is generally lower than 1% by weight, preferably lower than or equal to 0.5% by weight.

In still another embodiment, the eluting solvent is water for example fresh water as defined above.

The elution step can be carried out at a temperature which is usually greater than or equal to 20° C., preferably greater than or equal to 50° C. and most preferably greater than or equal to 80° C. This temperature is generally lower than or equal to 150° C. and preferably lower than or equal to 140° C.

After elution, the solvent used for eluting the metal salt can be recycled to the chlorination reactor.

Several steps of elution can be performed.

In particular after elution with the chlorohydrin the metal salt can then be optionally further eluted with an aqueous solution. The aqueous solution can arise from any step of the process. It is preferred to use fresh water as defined below.

The elution step can be carried out at a temperature which is usually greater than or equal to 20° C., preferably greater than or equal to 50° C. and most preferably greater than or equal to 80° C. This temperature is generally lower than or equal to 150° C. and preferably lower than or equal to 140° C.

After elution, the aqueous solution used for eluting the metal salt can be sent to the chlorination reactor, to a dehydrochlorination unit, to a biological treatment unit or to an oxidation treatment unit.

In a first variant, after elution with the chlorohydrin and water, the salt is removed as a solid in a suitable manner without further treatment. The salt is then disposed off in a suitable manner.

In a second variant, after elution with the chlorohydrin and water, the salt is dissolved with an aqueous solution.

The aqueous solution can arise from any step of the process. It is preferred to use fresh water as defined above.

The dissolution step can be carried out at a temperature which is usually greater than or equal to 20° C., preferably greater than or equal to 50° C. and most preferably greater than or equal to 80° C. This temperature is generally lower than or equal to 150° C. and preferably lower than or equal to 140° C.

The aqueous solution containing the dissolved metal salt can be disposed off. Preferably, it is sent to a dehydrochlorination unit, to a biological treatment unit or to an oxidation treatment unit.

In the above variants, the elution of the metal salt with water and the dissolution of the metal salt with water can be part of a single unit operation.

The above operations are particularly suited when the metal salt is sodium chloride or potassium chloride or sodium sulfate or potassium sulfate or any of their mixtures and more particularly suited for sodium chloride.

When the purge is carried out in a discontinuous mode, one filtration unit is usually sufficient since the filtration system can be regenerated during the shut-downs of the purge. When the purge is carried out in a continuous mode, it is preferred to have at least two filtration units working in alternance, one being in filtration mode while the other is in regeneration mode.

The filtration operation can be carried out in batch mode or continuous mode.

When anhydrous HCl is used as chlorinating agent, it is preferred to direct a liquid stream comprising the multihydroxylated-aliphatic hydrocarbon against the current of the stream of HCl. When the process is carried out in several reactors, the HCl is advantageously dried between two reactors, for example by adsorption on a suitable solid, such as a molecular sieve, or by reverse osmosis through a suitable membrane.

This particular embodiment of the process according to the invention makes it possible to obtain, particularly economically, a concentrated chlorhydrin often having a chlorohydrin content of greater than or equal to 90° A) by weight relative to the total weight of the chlorohydrin. When the chloroydrin is dichloropropanol, by means of this approach, it is possible to obtain 1,3-dichloropropane-2-ol as major isomer with an isomeric purity of greater than 80%.

In the process according to the invention, the mixture can contain the 1,3-dichloropropane-2-ol: and 2,3-dichloropropane-1-ol isomers in a mass ratio 1,3-dichloropropane-2-ol: 2,3-dichloropropane-1-ol generally higher than or equal to 0.5, often higher than or equal to 3, frequently higher than or equal to 7 and in particular higher than or equal to 20.

The invention is also related to a process for producing a chlorohydrin, according to which:
(a) a multihydroxylated-aliphatic hydrocarbon, an ester of a multihydroxylated-aliphatic hydrocarbon, or a mixture thereof, is subjected to a reaction with a chlorinating agent in a reaction medium
(b) continuous or periodic withdrawal from the reaction medium of a fraction comprising at least water and the chlorohydrin, is carried out
(c) at least part of the fraction obtained in step (b) is introduced into a distillation step
(d) the reflux ratio of the distillation step is controlled by supplying water to said distillation step.

The reaction medium is defined as above.

The fraction withdrawn at step (b) has a water content preferably higher than or equal to 12% by weight relative to the total weight of the withdrawn fraction.

The fraction withdrawn at step (b) may also contain hydrogen chloride. Preferably, the fraction is withdrawn continuously as its constituents form. The fraction obtained can subsequently be subjected to an operation of decantation after the distillation step.

The reaction medium of step (a) can be fed with water, in particular with steam. The feeding can be effected with extrinsic water originating from a suitable feed pipe or, optionally, with residual water recovered from another unit reaction or operation.

This feed is generally effected in such as way as to maintain the water concentration in the reaction medium within the ranges as described in patent application WO 2005/054167 in the name of SOLVAY SA from page 10, line 31 to page 11, line 11.

Continuous or periodic withdrawal can be carried out by introducing into a distillation step a gaseous phase, in particular withdrawing and introducing into a distillation step a gas phase which is in equilibrium with a liquid phase. A particular embodiment for the process according to the invention is to carry out steps (a) to (d) in a reactor surmounted by a suitable distillation column. Step (a) is carried out in the reactor. This embodiment is particularly suitable when aqueous hydrochloric acid is used as chlorinating agent. It is most particularly suitable when the chlorinating agent does not contain gaseous hydrogen chloride. In another embodiment for the process according to the invention, it is also possible to arrange a distillation column separated from the reactor, the liquid bottom of which can be sent back to the reaction medium. This embodiment is particularly suitable when hydrogen chloride, for example gaseous or essentially anhydrous hydrogen chloride, is used as chlorinating agent. Anhydrous hydrogen chloride has a water content which is generally lower than or equal to 40% by weight, preferably lower than or equal to 30% by weight and most preferably lower than or equal to 25% by weight. The water content of anhydrous hydrogen chloride is generally higher than or equal to 1 ppm by weight.

In one aspect, the fraction to be introduced into the distillation column separated from the reactor is withdrawn continuously or periodically, preferably continuously, from the liquid reaction mixture and at least water and the chlorohydrin is separated. In addition, one or more fractions containing organic products such as heavy byproducts and in particular catalyst and/or hydrogen chloride can also be separated in this distillation step and generally recycled to the reaction mixture. By selecting an appropriate reflux ratio, it is possible to separate in this aspect a fraction containing at least water which is substantially free of hydrogen chloride.

The reflux ratio can suitably be adjusted by supplying water which is preferably substantially free of hydrogen chloride to the distillation column. In this embodiment, the water is preferably fed to the top of the distillation column, Water can be supplied, for example by recycling at least a portion of water separated in the distillation operation to the top of the distillation column. Water can also be supplied by adding fresh water to the top of the distillation column. Both manners of supplying water can be combined. Adding fresh water gives particularly good results.

"Substantially free of hydrogen chloride", is understood to denote in particular a hydrogen chloride content in the fraction comprising water equal to or less than 10% by weight relative to the total weight of the fraction comprising water. Often, this content is equal to less than 5% by weight and preferably equal to or less than 1% by weight and more preferably equal to or less than 0.3% by weight. If hydrogen chloride is present in the fraction "substantially free of hydrogen chloride", its content is generally equal to or more than 1 mg/kg, often equal to or more than 5 mg/kg and in particular equal to or more than 10 mg/kg relative to the total weight of the fraction comprising water.

"Fresh" water is understood to denote water having a content of constituents other than water, organic or inorganic, lower than or equal to 12% by weight relative to the total weight of the water and of such constituents, preferably lower than or equal to 10% by weight and most preferably lower than or equal to 1% by weight. Generally, "fresh" water is understood to denote in particular water having a content of constituents other than water, organic or inorganic, equal to or more than 0.001 mg/kg, often equal to or more than 1 mg/kg relative to the total weight of water and of such constituents and frequently higher than or equal to 10 mg/kg. A possible source of fresh water can be for example the water used for eluting metal salt as described herein below, demineralized water obtained from ion-exchange resins, distilled water or water arising from steam condensation.

By constituents other than water, one intends to designate more specifically the chlorohydrin.

It has been found that the exploitation of the liquid-vapour equilibrium properties of the water-hydrogen chloride-chlorohydrin ternary composition makes it possible to withdraw from the production reaction the reaction products comprising in particular the chlorohydrin and water, while at the same time allowing most of the catalyst(s) and of the reactants (including the hydrogen chloride), to be recycled to the reactor, especially when the chlorohydrin is dichloropropanol.

The invention relates then also to a process for producing a chlorohydrin, according to which:
(a) a multihydroxylated-aliphatic hydrocarbon, an ester of a multihydroxylated-aliphatic hydrocarbon, or a mixture thereof, is subjected to a reaction with hydrogen chloride in a reaction mixture
(b) continuous or periodic withdrawal from the reaction mixture of a fraction comprising at least water, the chlorohydrin and hydrogen chloride, is carried out
(c) at least part of the fraction obtained in step (b) is introduced into a distillation step
wherein the ratio between the hydrogen chloride concentration and the water concentration of the fraction introduced into the distillation step is lower than the hydrogen chloride/water concentration ratio in the binary azeotropic composition hydrogen chloride/water at the temperature and pressure of the distillation.

This process is preferably carried out continuously.

In process according to the invention, the operating conditions of the reactor where the reaction between the multihydroxylated-aliphatic hydrocarbon, the ester of a multihydroxylated-aliphatic hydrocarbon, or the mixture thereof, and the chlorinated agent occurs, such as feed rates of reactants, in particular hydrogen chloride and the multihydroxylated-aliphatic hydrocarbon, the ester of a multihydroxylated-aliphatic hydrocarbon, or the mixture thereof, catalyst feed rate, temperature, reactor volume and pressure are preferably adjusted in such a way that the hydrogen chloride content of the fraction introduced into the distillation step is lower than the hydrogen chloride concentration in the binary azeotropic composition hydrogen chloride/water at the temperature and pressure of the distillation. An effective means of adjusting this concentration is controlling the hydrogen chloride supply to the liquid reaction medium.

It is possible for example to control the hydrogen chloride content in the fraction of step (b) by adding water. Such addition can be carried out for example by injection of vapor into the boiler of a distillation column used in the distillation step or by recycling to the distillation step of a water phase which can be obtained for example by decantation of a fraction withdrawn from the top of a distillation column, or by adding fresh water to the top of a distillation column or by adding a mixture of recycled and fresh water.

The maximum suitable hydrogen chloride concentration decreases slightly when the operating pressure is higher in agreement with the liquid-vapour equilibrium data for the azeotropic hydrogen chloride published by Bonner and Titus (J. Amer. Chem. Soc. 52, 633 (1930)) and partially reprinted in the Table hereafter:

| Pressure (Torr) | Temperature (° C.) | HCl in azeotrope (% wt) |
|---|---|---|
| 50 | 48.74 | 23.42 |
| 250 | 85.21 | 21.88 |
| 370 | 90.24 | 21.37 |
| 540 | 99.65 | 20.92 |
| 760 | 108.58 | 20.22 |
| 1000 | 116.19 | 19.73 |
| 1220 | 122.98 | 19.36 |

In such conditions, a fraction comprising water which fraction is substantially free of hydrogen chloride as defined above can be recovered by distillation from the reaction mixture or the gas phase above the liquid reaction mixture, e.g. by distilling material withdrawn from said gas phase and obtaining the fraction comprising water preferably at the top of the distillation column.

For instance, when the chlorohydrin is dichloropropanol, at atmospheric pressure (101.3 kPa), it is possible to obtain by distillation of the reactor gas phase a binary azeotropic mixture of water and dichloropropanol containing 23% by weight of dichloropropanol if the hydrogen chloride concentration in the total of the hydrogen chloride and water concentrations in that gas phase in contact with the reaction medium is lower than about 20.22% by weight.

In the process for producing the chlorohydrin according to the invention, the chlorohydrin can contain a high amount of halogenated ketones in particular chloroacetone as described in patent application FR 05.05120 of SOLVAY SA filed on May 20, 2005, the content of which is incorporated herein by reference. In the process for producing a chlorohydrin according to the invention, the halogenated ketone content of the chlorohydrin can be decreased by submitting the chlorohydrin to an azeotropic distillation in the presence of water or by submitting the chlorohydrin to a dehydrochlorination treatment, as described in patent application FR 05.05120 of SOLVAY SA filed on May 20, 2005.

Mention is particularly made of a process for manufacturing an epoxide in which halogenated ketones are formed as by-products and which comprises at least one treatment for the elimination of at least one part of the formed halogenated ketones. Mentions are more particularly made of a process for manufacturing an epoxide by dehydrochlorination of a chlorohydrin where at least a fraction of the chlorohydrin is manufactured by chlorination of a multi-hydroxylated aliphatic hydrocarbon, an ester of a multi-hydroxylated aliphatic hydrocarbon, or a mixture thereof, of a treatment of dehydrochlorination and of a treatment by azeotropic distillation of a mixture water-halogenated ketone, both treatments used in order to eliminate at least a part of the formed halogenated ketones and of a process for manufacturing epichlorohydrin in which the halogenated ketone is chloroacetone.

In the process for producing a chlorohydrin according to the invention, when the chlorohydrin is dichloropropanol, a high selectivity for 1,3-dichloropropane-2-ol is surprisingly obtained, which isomer is particularly suitable as starting product for a dehydrochlorination with a view to producing epichlorohydrin.

In the process according to the invention, the chlorohydrin can be submitted to a dehydrochlorination reaction to produce an epoxide, as described in patent applications WO 2005/054167 and FR 05.05120 in the name of SOLVAY SA In the process according to the invention, the chlorohydrin can be submitted to a dehydrochlorination reaction as described in patent application entitled <<Process for manufacturing an epoxide from a multi-hydroxylated aliphatic hydrocarbon and a chlorinating agent" filed in the name of SOLVAY SA on the same day as the present application, the content of which is incorporated herein by reference.

Mention is particularly made of a process for manufacturing an epoxide wherein a reaction mixture resulting from the reaction of a multi-hydroxylated aliphatic hydrocarbon, an ester of a multi-hydroxylated aliphatic hydrocarbon, or a mixture thereof, and a chlorinating agent, the reaction mixture containing less than 10 g of chlorohydrin per kg of the reaction mixture, is submitted to a further chemical reaction without intermediate treatment.

Mention is particularly made of a process for the manufacture of an epoxide comprising the following steps: (a) a multi-hydroxylated aliphatic hydrocarbon, an ester of a multi-hydroxylated aliphatic hydrocarbon, or a mixture thereof, is submitted to a reaction with a chlorinating agent and an organic acid in order to form a chlorohydrin and esters of chlorhydrin, in a reaction mixture containing, the multi-hydroxylated aliphatic hydrocarbon, the esters of multi-hydroxylated aliphatic hydrocarbon, water, the chlorinating agent and the organic acid, the reaction mixture containing at least 10 g of chlorohydrin per kg of the reaction mixture (b) at least one fraction of the mixture obtained in step, fraction which has the same composition as the reaction mixture obtained at step (a), is submitted to one or more treatment in steps subsequent to step (a), and (c) a basic compound is added at least one of the step subsequent to step (a) so as it reacts at least partially with the chlorohydrin, the esters of the chlorohydrin, the chlorinating agent and the organic acid in order to form an epoxide and salts.

The process for producing a chlorohydrin according to the invention can be integrated in a global scheme such as described in patent application entitled « Process for manufacturing an epoxide from a chlorohydrin" filed in the name of SOLVAY SA on on the same day as the present application, the content of which is incorporated herein by reference.

Mention is particularly made of a process for manufacturing an epoxide comprising at least one purification step of the formed epoxide, the epoxide being at least partially manufactured by a process of dehydrochlorination of a chlorohydrin, the chlorohydrin being at least partially manufactured by a process of chlorination of a multi-hydroxylated aliphatic hydrocarbon, of an ester of a multi-hydroxylated aliphatic hydrocarbon, or a mixture thereof.

When the chlorhydrin is dichloropropanol, the process of the invention can be followed by a manufacture of epichlorhydrin by dehydrochlorination of dicghloropropanol and the when the epoxide is epichlorohydrin, it can usefully be used for manufacturing epoxy resins.

FIG. 1 shows a preferred particular scheme for a plant that can be used for carrying out the process for producing a chlorohydrin according to the invention: A reactor (4) is fed, in a continuous or batch mode, with a multihydroxylated-aliphatic hydrocarbon, an ester of a multihydroxylated-aliphatic hydrocarbon, or a mixture thereof, via line (1) and catalyst via line (2), the feed of the chlorinating agent, is carried out continuously or in batch-mode via line (3), a distillation column (6) is fed via line (5) with vapour produced from reactor (4), a stream is withdrawn from column (6) via line (7) and fed to a condenser (8), the stream from the condenser is fed via line (9) to a decanter (10) in which aqueous and organic phases are separated. A fraction of the separated aqueous phase is optionally recycled via line (11) to the top of the column for maintaining reflux. Fresh water can be added via line (12) to the top of the column for maintaining reflux. The production of the chlorohydrin is distributed between the organic phase withdrawn through line (14) and the aqueous phase withdrawn through line (13). The residue from column (6) can be recycled to the reactor via line (15). Heavy by-products can optionally be removed from the reactor by means of a purge (16) located in the liquid bottom of the reactor. A stream is withdrawn from the purge (16) and fed via line (17) into an evaporator (18) wherein a partial evaporation operation is carried out e.g. by heating or by gas sweeping with nitrogen or steam, the gas phase containing most of the chlorinating agent from stream (17) is recycled via line (19) to the column (6) or via line (20) to the reactor (4), a distillation column or stripping column (22) is fed with the liquid phase arising from the evaporator (18) via line (21), the main fraction of the chlorohydrin is collected from the top of the column (22) through line (23) and the column residue is fed via line (24) to a filtration unit (25) in which solid and liquid phases are separated, the liquid phase is recycled via line (26) to the reactor (4). The solid can be withdrawn from the filtration unit (25) via line (27) as a solid or as a solution. Solvents can be added to the filtration unit (25) via lines (28) and (29) for washing and/or dissolution of the solid and withdrawn from line (27). Optionally, a stream is withdrawn from the purge (16) and fed via line (30) into a filtration column (25). The stripper (18) and the distillation column (22) are then bypassed.

Results obtained according to this last scheme (stripper (18) and column (22) bypassed) are detailed in example 1.

The process described above is well suited when the multihydroxylated-aliphatic hydrocarbon is ethylene glycol, propylene glycol and glycerol, the chlorohydrine is chloroethanol, chloropropanol, chloropropanediol and dichloropropanol and the epoxide is ethylene oxide, propylene oxide, glycidol and epichlorohydrin and the chlorinating agent is hydrogen chloride, anhydrous or in aqueous solution. The process is particularly convenient when the multihydroxylated-aliphatic hydrocarbon is glycerol, the chlorohydrin is dichloropropanol and the epoxide is epichlorohydrin.

When the multihydroxylated-aliphatic hydrocarbon is glycerol, this variant of the process allows to remove at the top by azeotropy almost all of the water arising from the reaction, from the starting materials and/or possibly fed in the bottom of the reactor or of the column and to obtain a mixture of dichloropropanols of very high purity, above 99.5% by weight for the sum of the two isomers, with a selectivity related to hydrocarbon chain and hydrogen chloride higher than 99% by weight and to remove the metal salt which can build up in the reactor when crude glycerol is used in the reaction.

The example below are intended to illustrate the invention without, however, limiting it.

EXAMPLE 1

The numbers in parentheses refer to FIG. 1. The additional equipment in the schema of FIG. 1, with stripper (18) and column (22) has not been used in this case.

Reactor (4) has been continuously fed with crude glycerol and a 33% by weight hydrochloric aqueous acid solution with relative flow rates mass ratios of 2.06. The crude glycerol was a by product of the biodiesel production and contained 85% of glycerol, 6% of NaCl and 0.5% of organic impurities (fatty acids and derivatives). The residence time was 16 h, the adipic acid concentration in the reaction medium was 2.5 mol of acid functionalities/kg. The reactor has been operated at atmospheric pressure and at 115° C. The reaction mixture has been stripped with of nitrogen and the generated vapor phase has been treated in the distillation column (6) via line (5) (FIG. 1). The gas phase removed from column (6) has been condensed at 25° C. (8) and decanted in the decanter (10). Reflux ratio was adjusted to withdraw the entire production of dichloropropanol at the top of column by recycling an appropriate amount of the aqueous phase from the decanter. At the outlet of the decanter an aqueous phase containing 15.0% of dichloropropanol (13) and an organic phase (14) containing 88% of dichloropropanol were recovered. The profiles in organic impurities in these phases were not different from those observed when pure glycerol is used in the process.

A slurry from the reactor has been pumped on a 115 micrometer PTFE membrane filter in the filtration column (25). The salt cake in the filter has been washed at 20° C. with dichloropropanol saturated with water. After removal of the liquid phase and draining of the solid, the salt has been dissolved in water and the salted water phase has been discarded. The duration of washing and salt dissolution was about 2 hours. A new filtration cycle of the slurry from the reactor has then been operated. The dichloropropanol washing has been recycled to the reactor by continuous feeding. The analysis of the water phase with salt indicated a dichloropropanol:NaCl mass ratio of 1.44 and a small amount of catalyst (less than 10 g/kg). The quantity of dichloropropanol in the salted water represented 1.6% of the dichloropropanol total production.

The global yield in dichloropropanol was 93%.

The invention claimed is:

1. A process for producing dichloropropanol, comprising reacting glycerol with a chlorinating agent, wherein the reaction is carried out in a reaction mixture comprising glycerol that has at least one solid or dissolved metal salt therein in a positive amount of up to at most 15% by weight, the process further comprising submitting at least a fraction of the reaction mixture to a treatment comprising a separation operation to remove at least part of the metal salt from said fraction.

2. The process according to claim 1, wherein the glycerol has at least partially been obtained from renewable raw materials.

3. The process according to claim 1, wherein the metal salt is selected from sodium chloride, potassium chloride, sodium sulfate and potassium sulfate.

4. The process according to claim 1 wherein the glycerol has from 0.5 to 15% by weight of metal salt therein.

5. The process according to claim 1 wherein the chlorinating agent is gaseous hydrogen chloride.

6. The process according to claim 1 wherein the reaction is carried out in the presence of a catalyst, wherein the catalyst is a carboxylic acid.

7. The process according to claim 6 wherein the carboxylic acid has an atmospheric boiling point of greater than or equal to 200° C.

8. The process according to claim 1 wherein the separation operation is selected from liquid/solid, liquid/liquid, liquid/gas and solid/gas separation.

9. The process according to claim 8 wherein the separation operation is selected from liquid/solid, liquid/liquid, and liquid/gas separation, and wherein the liquid/solid separation operation is selected from decantation, centrifugation, filtration, adsorption and treatment with ion-exchanged resins, the liquid/liquid separation operation is selected from decantation and centrifugation, and the liquid/gas separation operation is selected from stripping, evaporation and distillation.

10. The process according to claim 9 wherein the separation operation is selected from liquid/solid, the liquid/solid separation operation is filtration, and the metal salt is removed as a solid.

11. The process according to claim 1 wherein the fraction of the reaction mixture is submitted to a treatment to remove at least one component other than the metal salt prior to the separation operation, and wherein the treatment is a stripping or a distillation operation.

12. The process according to claim 1, carried out continuously.

13. The process according to claim 1, further comprising manufacturing epichlorohydrin by dehydrochlorination of the dichloropropanol.

14. The process according to claim 13, further comprising manufacturing an epoxy resin by reacting the epichlorohydrin.

15. The process according to claim 1 wherein the glycerol has from 0.5 to 7.5% by weight of metal salt therein.

16. The process according to claim 1 wherein the glycerol has from 0.5 to 5% by weight of metal salt therein.

17. The process according to claim 1 wherein the glycerol has from 3 to 7.5% by weight of metal salt therein.

18. The process according to claim 1 wherein the glycerol has from 3 to 5% by weight of metal salt therein.

* * * * *